(12) United States Patent
Jackson et al.

(10) Patent No.: US 11,974,864 B2
(45) Date of Patent: May 7, 2024

(54) STACKABLE ENDOSCOPE STORAGE TRAY AND METHOD OF USE

(71) Applicant: Medivators Inc., Minneapolis, MN (US)

(72) Inventors: Mark Jackson, Great Wakering (GB); Gary Spencer, Rayleigh (GB); Lindani Phungula, Southend on Sea (GB)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 17/801,338

(22) PCT Filed: Feb. 18, 2021

(86) PCT No.: PCT/US2021/018463
§ 371 (c)(1),
(2) Date: Aug. 22, 2022

(87) PCT Pub. No.: WO2021/173405
PCT Pub. Date: Sep. 2, 2021

(65) Prior Publication Data
US 2023/0082582 A1 Mar. 16, 2023

Related U.S. Application Data

(60) Provisional application No. 62/981,138, filed on Feb. 25, 2020.

(51) Int. Cl.
*A61B 50/33* (2016.01)
*A61B 50/13* (2016.01)
(Continued)

(52) U.S. Cl.
CPC .............. *A61B 50/33* (2016.02); *A61B 50/13* (2016.02); *B65D 21/0223* (2013.01);
(Continued)

(58) Field of Classification Search
CPC ......... A61B 50/33; A61B 50/30; A61B 50/13; A61B 50/10; A61B 2050/105;
(Continued)

(56) References Cited

U.S. PATENT DOCUMENTS

| 803,102 A | 10/1905 | Harris |
| 1,592,726 A | 7/1926 | Dunbar |

(Continued)

FOREIGN PATENT DOCUMENTS

| AU | 2018211256 A1 | 2/2019 |
| CN | 108030556 A | 5/2018 |

(Continued)

OTHER PUBLICATIONS

ARES flexible endoscope automated reprocessing system' (Steelco) Jul. 12, 2018 (Dec. 7, 2018) [retreived from the internet on Aug. 24, 2020 (Aug. 24, 2020) at https://web.archive.org/web/20180712214831/http://www.peacocks.net/_filecache/9e4/a6e/550-steelco-ares-rev04.pdf].

(Continued)

*Primary Examiner* — Javier A Pagan

(57) ABSTRACT

An endoscope tray is provided. The tray comprises an interior for storage of an endoscope. The tray has a lid configured to cover the tray. The lid has an exterior surface having a recess and/or projection, and the tray has a bottom exterior surface having a recess and/or projection such that the recess and/or projection of the lid is configured to mate with the recess and/or projection of the bottom exterior surface of the tray. Systems and methods are also provided.

5 Claims, 24 Drawing Sheets

(51) Int. Cl.
  *B65D 21/02* (2006.01)
  *A61B 50/00* (2016.01)
  *A61B 50/30* (2016.01)

(52) U.S. Cl.
  CPC . *A61B 2050/006* (2016.02); *A61B 2050/3007* (2016.02); *A61B 2050/3011* (2016.02); *A61B 2050/314* (2016.02)

(58) Field of Classification Search
  CPC ...... A61B 2050/3007; A61B 2050/314; B65D 21/0223; B65D 21/2017; B65D 21/0215; B65D 21/0209
  See application file for complete search history.

(56) References Cited

U.S. PATENT DOCUMENTS

| | | | |
|---|---|---|---|
| 1,717,974 A | 6/1929 | Heinrichs | |
| 2,080,108 A | 5/1937 | Bradstein | |
| 2,214,946 A | 9/1940 | Werner | |
| 2,412,325 A | 12/1946 | Devine et al. | |
| 3,157,902 A | 11/1964 | Hardwick | |
| 3,757,990 A | 9/1973 | Buth | |
| 3,770,119 A | 11/1973 | Hultberg et al. | |
| 3,949,934 A | 4/1976 | Goglio | |
| 4,042,109 A | 8/1977 | Barcan | |
| 4,053,280 A | 10/1977 | Salisbury | |
| 4,256,225 A | 3/1981 | Jackson | |
| 4,466,552 A | 8/1984 | Butterworth et al. | |
| 4,574,978 A | 3/1986 | Hodges | |
| 4,583,643 A | 4/1986 | Sanderson | |
| 4,750,619 A | 6/1988 | Cohen et al. | |
| 4,754,595 A | 7/1988 | Sanderson | |
| 4,948,266 A | 8/1990 | Bencic | |
| 5,108,195 A | 4/1992 | Perron | |
| 5,207,325 A | 5/1993 | Kennedy | |
| 5,295,606 A | 3/1994 | Karwoski | |
| 5,392,917 A | 2/1995 | Alpern et al. | |
| 5,409,126 A | 4/1995 | Demars | |
| 5,443,801 A | 8/1995 | Langford | |
| 5,882,589 A | 3/1999 | Mariotti | |
| 5,989,608 A | 11/1999 | Mizuno | |
| 6,029,844 A | 2/2000 | Brady | |
| 6,139,185 A | 10/2000 | Hamilton et al. | |
| 6,151,910 A | 11/2000 | Hazen | |
| 6,210,638 B1 | 4/2001 | Grieco et al. | |
| 6,235,692 B1 | 5/2001 | Scoville et al. | |
| 6,305,567 B1 | 10/2001 | Sulpizio | |
| 6,378,721 B1 | 4/2002 | Williams | |
| 6,380,524 B1 | 4/2002 | Keller | |
| 6,622,862 B1 | 9/2003 | Corrado | |
| 6,622,864 B1 | 9/2003 | Debbs et al. | |
| 6,641,781 B2 | 11/2003 | Walta | |
| 6,733,803 B1 | 5/2004 | Karsten | |
| 6,749,063 B2 | 6/2004 | Parker | |
| 6,994,823 B2 | 2/2006 | Hight, III | |
| 7,041,941 B2 | 5/2006 | Faries, Jr. et al. | |
| D531,734 S | 11/2006 | Haunschild et al. | |
| 7,630,791 B2 | 12/2009 | Nguyen et al. | |
| 8,287,816 B2 | 10/2012 | Kral | |
| 8,414,471 B2 | 4/2013 | Mandava et al. | |
| 8,435,445 B2 | 5/2013 | Kral | |
| 8,454,901 B1* | 6/2013 | Snyder, III | A61L 2/26 422/26 |
| 8,733,551 B2 | 5/2014 | Parker et al. | |
| 8,795,603 B2 | 8/2014 | Ghelman et al. | |
| 8,851,287 B2 | 10/2014 | Becklin | |
| 8,905,258 B2 | 12/2014 | Javid et al. | |
| 9,348,013 B2 | 5/2016 | Rahim et al. | |
| 9,703,264 B2 | 7/2017 | Freijsen et al. | |
| 9,910,965 B2 | 3/2018 | Bufalini et al. | |
| D818,841 S | 5/2018 | Newton | |
| D819,409 S | 6/2018 | Newton | |
| 10,405,938 B2 | 9/2019 | Ramsey | |
| 10,418,831 B2 | 9/2019 | Racenet et al. | |
| 10,456,494 B2 | 10/2019 | Roudebush et al. | |
| 10,463,441 B2 | 11/2019 | Tate et al. | |
| D909,883 S | 2/2021 | Newton | |
| D921,490 S | 6/2021 | Newton | |
| 11,445,900 B2 | 9/2022 | King et al. | |
| 11,696,811 B2 | 7/2023 | Dalena et al. | |
| 2003/0078472 A1 | 4/2003 | Parker | |
| 2004/0101456 A1 | 5/2004 | Kuroshima et al. | |
| 2007/0215507 A1 | 9/2007 | Glenn et al. | |
| 2007/0228080 A1 | 10/2007 | Lin et al. | |
| 2008/0251102 A1 | 10/2008 | Haack et al. | |
| 2009/0091453 A1 | 4/2009 | Ishida et al. | |
| 2009/0206674 A1 | 8/2009 | Noguchi et al. | |
| 2010/0176016 A1 | 7/2010 | Pell | |
| 2010/0189598 A1 | 7/2010 | Fraundorfer | |
| 2011/0002811 A1 | 1/2011 | Dane et al. | |
| 2011/0192744 A1* | 8/2011 | Parker | A61B 50/30 206/363 |
| 2012/0152289 A1 | 6/2012 | Smith et al. | |
| 2013/0019910 A1 | 1/2013 | Ledel | |
| 2013/0105344 A1 | 5/2013 | Hartley | |
| 2013/0192647 A1 | 8/2013 | Ledel et al. | |
| 2014/0069841 A1 | 3/2014 | Pizzato et al. | |
| 2014/0083886 A1 | 3/2014 | Winterrowd et al. | |
| 2014/0182629 A1 | 7/2014 | Dromard et al. | |
| 2014/0270583 A1* | 9/2014 | Anderson | B65D 33/001 383/37 |
| 2014/0339114 A1 | 11/2014 | Griffin | |
| 2014/0353203 A1 | 12/2014 | Hu et al. | |
| 2015/0259122 A1 | 9/2015 | Parker | |
| 2015/0272680 A1 | 10/2015 | Suzuki | |
| 2016/0058900 A1 | 3/2016 | Sato | |
| 2016/0095508 A1 | 4/2016 | Terliuc et al. | |
| 2016/0249915 A1 | 9/2016 | Beckman et al. | |
| 2017/0056122 A1 | 3/2017 | Ramsey | |
| 2017/0091389 A1 | 3/2017 | Dukatz | |
| 2018/0028703 A1* | 2/2018 | McLaughlin | A61B 50/34 |
| 2018/0071045 A1 | 3/2018 | Cohen et al. | |
| 2018/0134453 A1* | 5/2018 | Wassenburg | A61B 50/30 |
| 2019/0365500 A1 | 12/2019 | Erdmann et al. | |
| 2020/0118674 A1 | 4/2020 | Le et al. | |
| 2020/0187767 A1 | 6/2020 | Kramer et al. | |
| 2020/0205925 A1 | 7/2020 | Cummings et al. | |
| 2020/0315731 A1 | 10/2020 | Zardini et al. | |
| 2021/0076923 A1 | 3/2021 | Awau | |
| 2021/0128768 A1 | 5/2021 | Jackson et al. | |
| 2021/0138517 A1 | 5/2021 | Kakar et al. | |
| 2021/0186641 A1 | 6/2021 | Cummings et al. | |
| 2021/0187141 A1 | 6/2021 | Crotti | |
| 2021/0212796 A1 | 7/2021 | Crotti | |
| 2021/0356051 A1 | 11/2021 | Gray-Dreizler et al. | |
| 2022/0211458 A1 | 7/2022 | Jackson et al. | |
| 2022/0304560 A1 | 9/2022 | Jackson et al. | |
| 2022/0304762 A1 | 9/2022 | Jackson et al. | |
| 2022/0304764 A1 | 9/2022 | Jackson et al. | |
| 2022/0387651 A1 | 12/2022 | Kendrick | |
| 2022/0392102 A1 | 12/2022 | Ohara et al. | |
| 2023/0082582 A1 | 3/2023 | Jackson et al. | |
| 2023/0285614 A1 | 9/2023 | Kotani et al. | |

FOREIGN PATENT DOCUMENTS

| | | |
|---|---|---|
| DE | 202016105248 | 12/2016 |
| EP | 0091792 B1 | 1/1988 |
| EP | 0830295 A1 | 3/1998 |
| EP | 2689706 A2 | 1/2014 |
| EP | 2900117 A1 | 8/2015 |
| JP | 2007054343 | 3/2007 |
| JP | 2009172228 | 8/2009 |
| JP | 2008054861 | 3/2020 |
| WO | 9607364 | 3/1996 |
| WO | 2011151641 | 12/2011 |

(56) References Cited

FOREIGN PATENT DOCUMENTS

| WO | 2018024690 | | 2/2018 |
|---|---|---|---|
| WO | 2018152400 | A1 | 8/2018 |

OTHER PUBLICATIONS

International Preliminary Report on Patentability dated Dec. 30, 2021, of International PCT Application No. PCT/ US/2020/036618 dated Jun. 8, 2020.
International Search Report and Written Opinion of the International Searching Authority dated Sep. 9, 2020, of International PCT Application No. PCT/US2020/036618 filed Jun. 8, 2020.
Steelco ED200 Endoscope Drying/Storage Cabinet' (Peacocks Medical Group) Jun. 20, 2018(Jun. 28, 2018) [retreived from the internet on Aug. 24, 2020 (Aug. 24, 2020) at https://web.archive.org/web/20180620034054/https://www.peacocks.net/medical-decontamination/endoscopy/endoscopy-drying-cabinetslsteelco-ed200.
International Preliminary Report on Patentability dated Dec. 30, 2021, of International PCT Application No. PCT/US/2020/036630 dated Jun. 8, 2020.
International Preliminary Report on Patentability dated Dec. 30, 2021, of International PCT Application No. PCT/US/2020/036635 dated Jun. 8, 2020.
International Preliminary Report on Patentability dated Sep. 9, 2022 of International PCT Application No. PCT/US/2021/018463 dated Feb. 18, 2021.
International Preliminary Report on Patentability dated Sep. 30, 2021, of International PCT Application No. PCT/US2020/019640, dated Feb. 25, 2020.
International Search Report and Written Opinion dated May 6, 2021, in International Application No. PCT/US2021/018463 filed Feb. 18, 2021.
International Search Report and Written Opinion dated Nov. 20, 2020, in International Application No. PCT/US2020/036635 filed Jun. 8, 2020.
International Search Report and Written Opinion of the International Searching Authority dated Jun. 5, 2020, of International PCT Application No. PCT/US2020/019640 filed Feb. 25, 2020.
International Search Report and Written Opinion of the International Searching Authority dated Sep. 3, 2020, of International PCT Application No. PCT/US2020/036630 filed Jun. 8, 2020.

\* cited by examiner

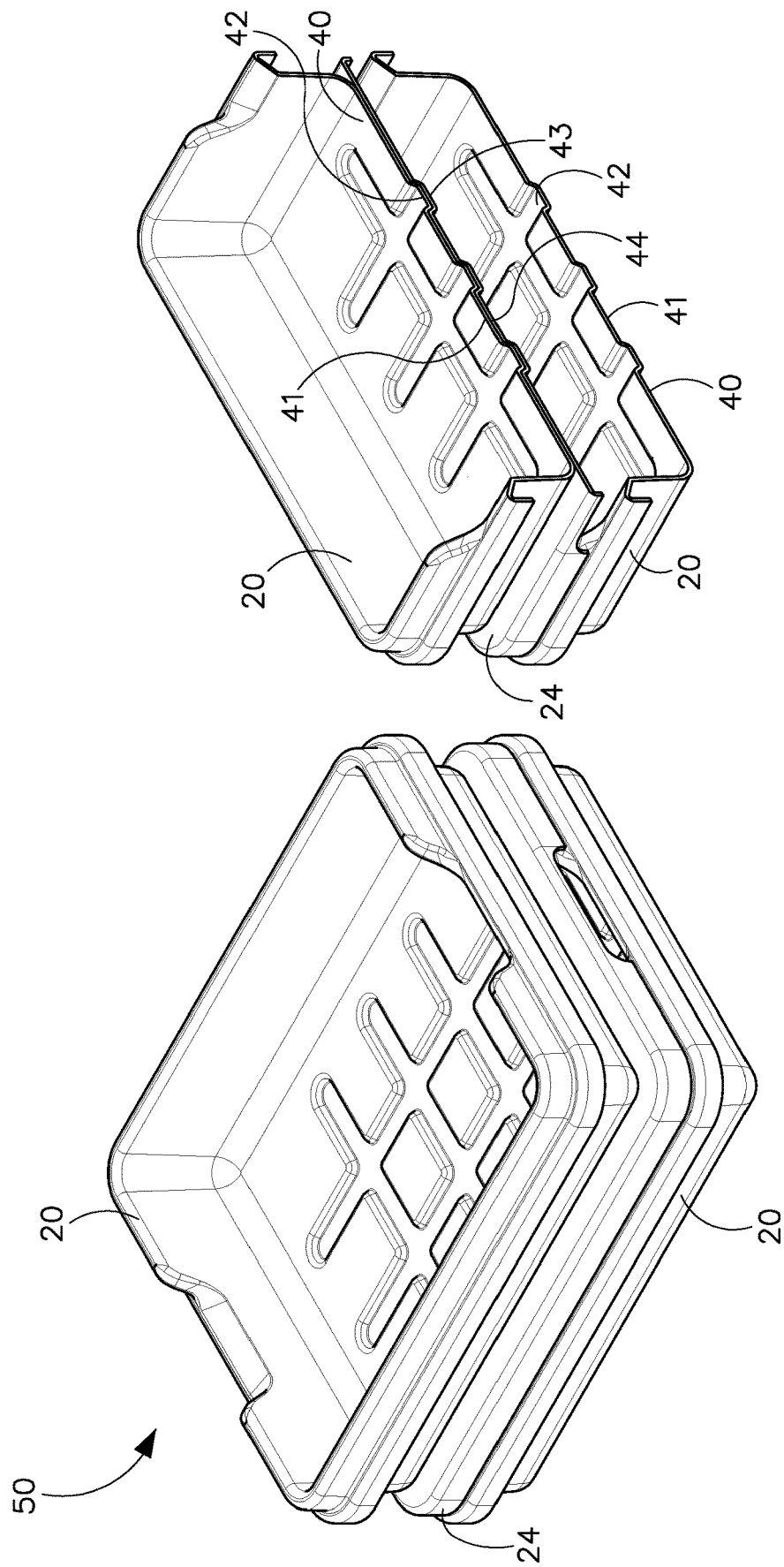

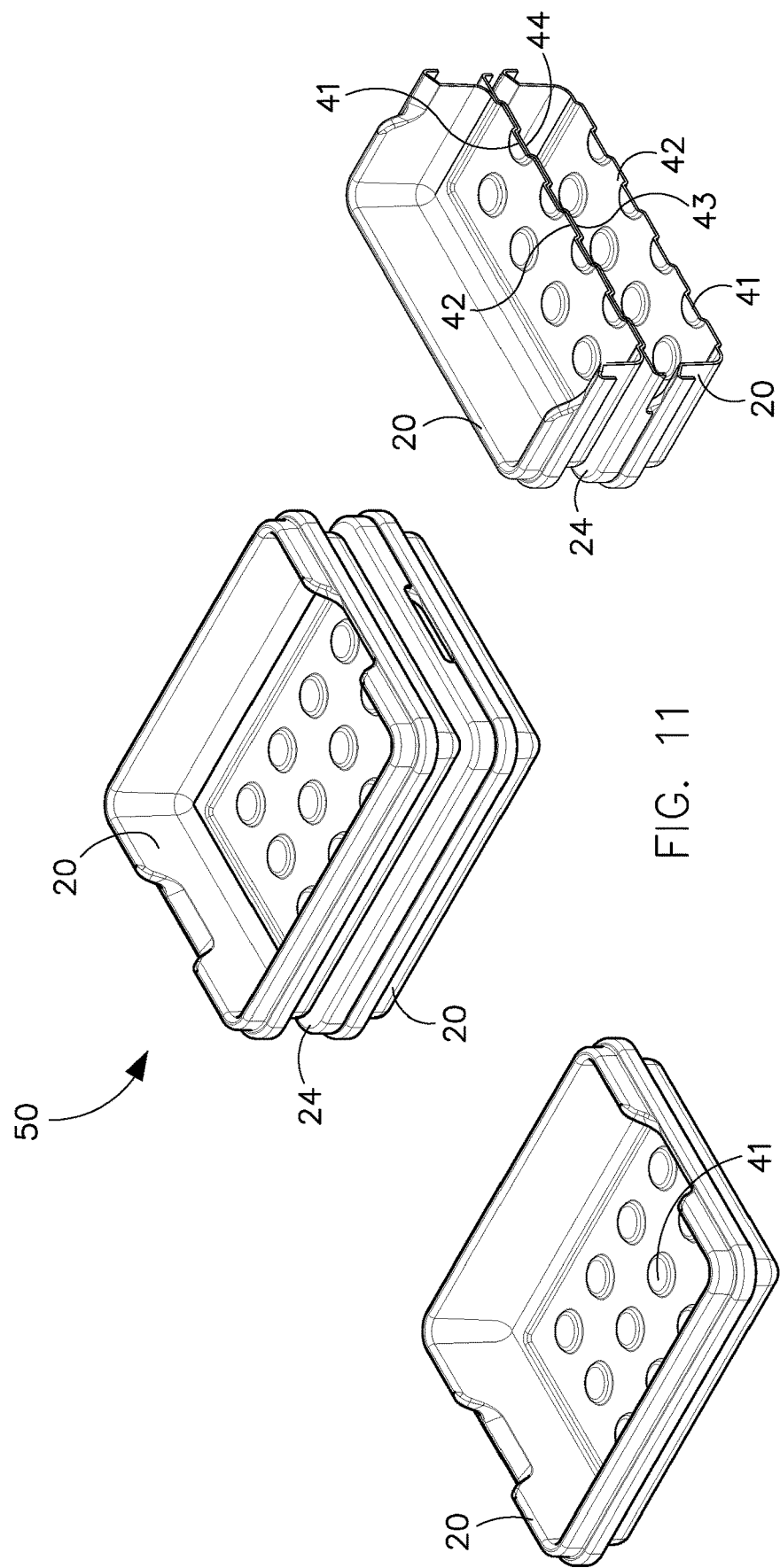

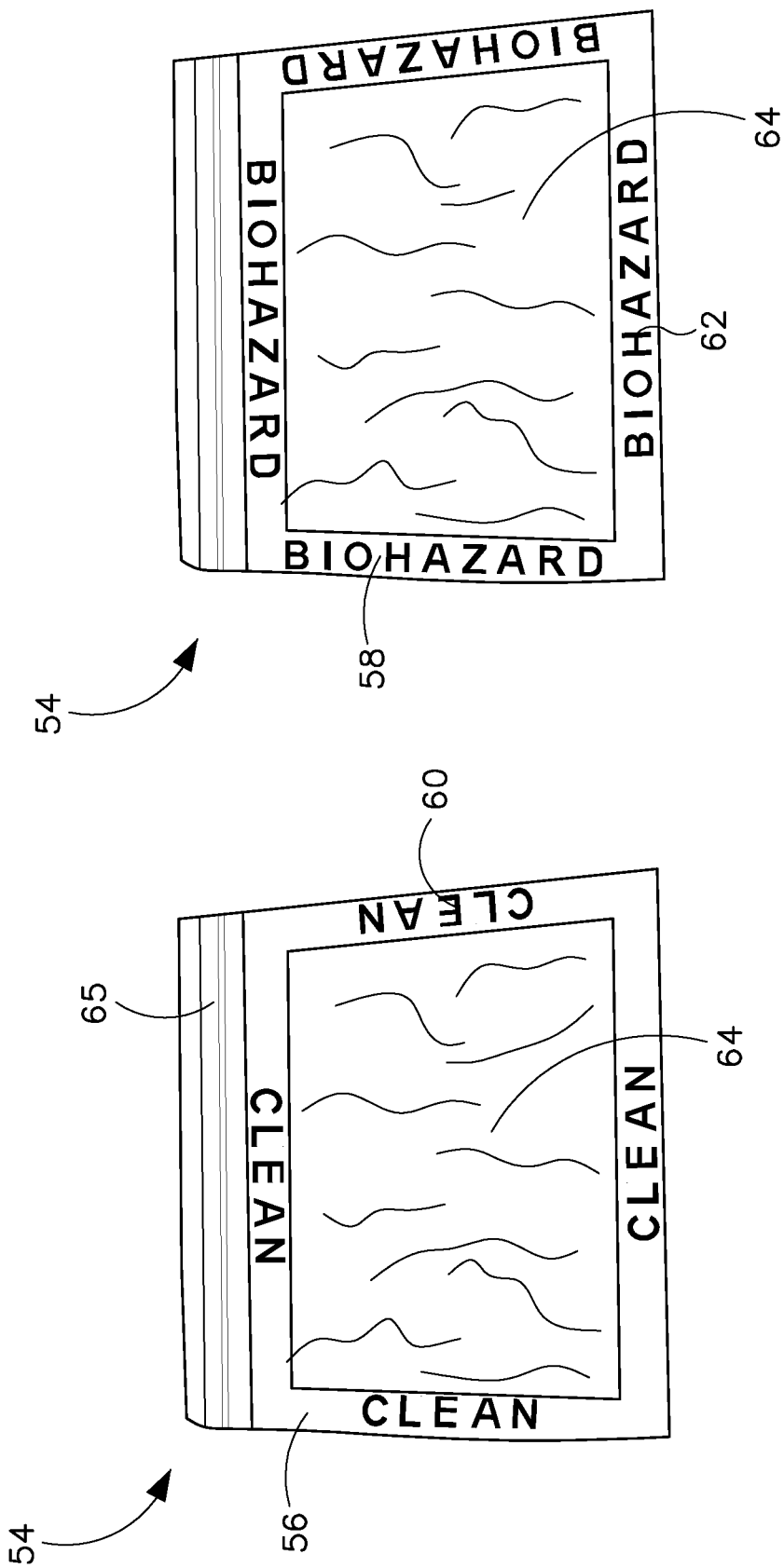

STACKABLE ENDOSCOPE STORAGE TRAY AND METHOD OF USE

PRIORITY CLAIM

This application claims priority to and the benefit of U.S. Provisional application with Ser. No. 62/981,138, filed on Feb. 25, 2020, entitled STACKABLE ENDOSCOPE STORAGE TRAY AND METHOD OF USE, which is herein incorporated by reference in its entirety.

BACKGROUND

Endoscopes are well-known in the art and are commonly used for numerous medical procedures. After each use, an endoscope will undergo reprocessing by cleaning, disinfection and/or sterilization to reduce or prevent contaminants from settling onto the endoscope, as well as to prevent the spread of disease, viruses, bacteria, and illness.

After endoscope reprocessing, an endoscope is generally disposed in a stress-free state within a clean tray that has been cleaned in a cart washer, where fluid, chemicals and/or heat are applied to the tray in order to decontaminate the tray. However, due to high temperatures, trays can deform during washing. After the endoscope has been disposed within the clean tray, a cover and/or a lid can be secured to the perimeter of the tray. The tray can then be stacked one on top of another where it can be then transported by hand or stacked in a cart and then transported to a procedure or storage room. After the endoscope is used, or the shelf-life of the contents of the tray has expired, the tray can be stacked one on top of the other and transported back for reprocessing.

During transport, the stacked trays can move, increasing the chances of the endoscopes stored within the trays being damaged. Further, movement of the stacked trays can make transport more difficult since the stacked trays may slide with side to side movement. This side to side or lateral movement may cause damage to the endoscope during transport. If one or more trays fall, the endoscope can be further damaged or the endoscope may be placed in a different tray all together, which may lead to difficulties in tracking the endoscope before or after use and risk potential cross-contamination among patients undergoing an endoscope procedure. While some known brands of trays can be stacked, these trays are not locked together in a mating engagement to prevent movement.

Thus, there is a need to develop a new tray, systems and methods where endoscope trays can be stacked in a mating engagement to lock the trays together to improve tray portability during transport and storage. There is also a need to provide stackable trays that reduce side to side movement of the trays when transported. There is also a need to develop a tray that is cart washer compatible so that the tray does not deform during washing.

SUMMARY

New devices, systems and methods are provided to facilitate the stacking of endoscope trays that are configured to matingly engage on top of each other, locking the trays together to reduce movement, in particular, lateral side to side movement during storage and transport. In some embodiments, an endoscope tray is provided. The tray comprises an interior for storage of an endoscope. The tray has a lid configured to cover the tray. The lid has an exterior surface having a recess and/or projection, and the tray has a bottom exterior surface having a recess and/or projection such that the recess and/or projection of the lid is configured to mate with the recess and/or projection of the bottom exterior surface of the tray.

In some embodiments, a stackable tray system for storage of endoscopes is provided. The system comprises a first tray comprising an interior for storage of a first endoscope. The first tray has a first lid configured to cover the first tray. The first lid has an exterior surface having a recess and/or projection, and the first tray has a bottom exterior surface having a recess and/or projection. A second tray is provided comprising an interior for storage of a second endoscope. The second tray has a second lid configured to cover the second tray. The second lid has an exterior surface having a recess and/or projection, and the second tray has a bottom exterior surface having a recess and/or projection. The recess and/or projection of the exterior surface of the first lid of the first tray is configured to mate with the recess and/or projection of the bottom exterior surface of the second tray when the first tray and the second tray are stacked together to reduce lateral side to side movement of the first tray and the second tray.

In some embodiments, a method of using stackable endoscope storage trays is provided. The method comprising placing a first endoscope within a first tray, the first tray comprising an interior for storage of the first endoscope, the first tray having a first lid configured to cover the first tray, the first lid having an exterior surface having a recess and/or projection, and the first tray having a bottom exterior surface having a recess and/or projection; covering the first tray with the first lid; placing a second endoscope within a second tray, the second tray comprising an interior for storage of the second endoscope, the second tray having a second lid configured to cover the second tray, the second lid having an exterior surface having a recess and/or projection, and the second tray having a bottom exterior surface having a recess and/or projection; covering the second tray with the second lid; and stacking the recess and/or projection of the bottom exterior surface of the second tray on the recess and/or projection of the exterior surface of the first lid to mate the second tray with the first lid to reduce side to side movement of the first tray and the second tray.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings.

FIG. 5 illustrates a perspective view of the tray and lid of FIG. 1 stacked with a second tray.

FIG. 6 illustrates a perspective cross section view of the stacked configuration of FIG. 5.

FIG. 10 illustrates a perspective view of the tray without the lid of FIG. 9.

FIG. 11 illustrates a perspective view of the tray and lid of FIG. 9 stacked with a second tray.

FIG. 12 illustrates a perspective cross section view of the stacked configuration of FIG. 9.

FIG. 29 illustrates a top perspective view of the flexible cover in a bag configuration with the term "clean" written on the cover to indicate a clean cover. In this embodiment of the cover, the cover can be a green color.

FIG. 30 illustrates a top perspective view of the flexible cover in a bag configuration with the term "biohazard" written on the cover to indicate a dirty cover. In this embodiment of the cover, the cover can be a red color.

Figure 1:
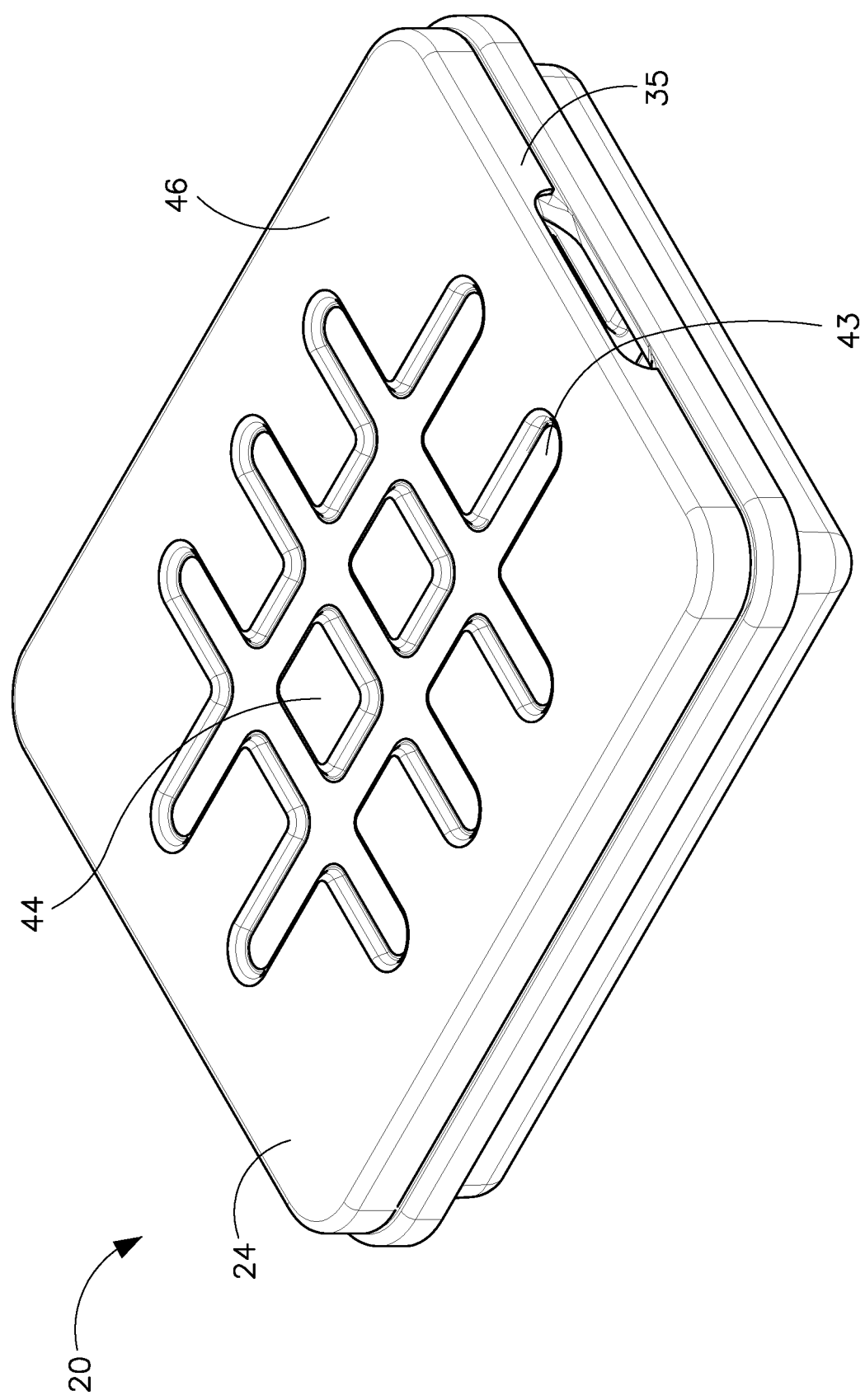
FIG. 1 illustrates a perspective view of an endoscope tray. The tray comprises an interior for storage of an endoscope and a lid configured to cover the tray. The lid has an exterior surface having a pattern shaped recess and projections, and the tray has a bottom exterior surface having recesses and a pattern shaped projection such that the pattern shaped recess and the projections of the lid are configured to mate with the recesses and pattern shaped projection of the bottom exterior surface of the tray.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including)

the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "outlet" includes one, two, three or more outlets.

We refer now to the drawings wherein depicted elements are not necessarily shown to scale and wherein like or similar elements are designated by the same reference numeral through the several views.

The term "recess" or "recesses" refers to a cavity that can be defined from a bottom exterior surface of the tray or that can be defined from an exterior surface of the lid.

The term "projection" or "projections" refers to a raised portion that projects outwardly and is defined from a bottom exterior surface of the tray or an exterior surface of the lid. It is to be understood that a projection defined from the tray will mate with a corresponding recess defined from the lid and a recess defined from the tray will mate with a corresponding projection defined from the lid.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

In some embodiments, a tray is provided that has a feature such as a recess and/or a projection within a base of the tray and on an upper surface of a lid to allow for tray and lid engagement. This engagement or interface between the tray and the lid will prevent sliding of the base of the tray on the upper surface of the lid which will improve portability. In some embodiments, the recess and/or projection on the tray will also provide increased strength to the base of the tray and the recess and/or projection on the lid will provide increased strength to the lid to decrease the likelihood of tray and lid deformation during a cart washing cycle at elevated temperatures.

In some embodiments, a tray is provided that is cart washer compatible and that is chemical and heat resistant. In some embodiments, dimensions of the tray can be sufficient to accommodate substantially all sizes of flexible medical endoscopes in a coiled state without undue stress being applied to the flexible portions of the endoscope. However, the tray can also be sufficiently small to permit it to be easily carried by a person. In some embodiments, the tray is constructed and dimensioned to provide support for the endoscope coiled in a stress-free state.

In some embodiments, the tray is rigid and re-usable and comprises a base having planar and non-planar portions and surrounding sidewalls upstanding therefrom, the tray being formed of a semi-rigid material capable of withstanding repeated disinfection and dimensioned to provide support for a flexible medical endoscope coiled in a stress-free state.

In some embodiments, the tray is designed to prevent contact of sensitive areas of an endoscope from coming into contact with each other during storage and transportation which prevents damage to the endoscope.

Tray

Referring to FIGS. 1-21, an endoscope tray 20 is provided. The tray is configured to store a flexible medical endoscope 22 and to be matingly stacked with other compatible trays having a corresponding lid 24 to improve stability and portability during transport. The tray can be rigid and reusable and can be formed of a semi-rigid material capable of withstanding repeated disinfection and dimensioned to provide support for the endoscope coiled in a stress-free state.

Figure 2:
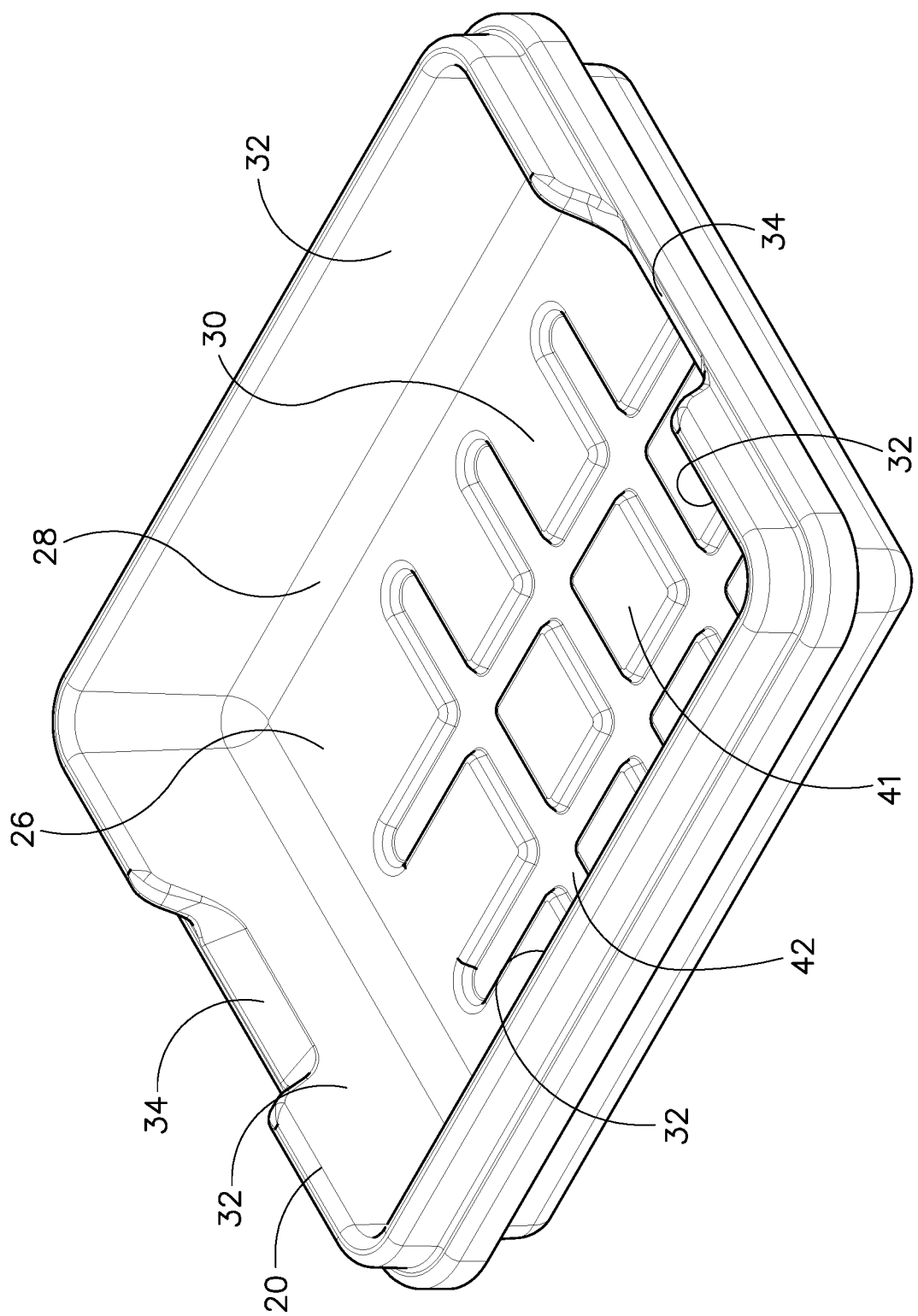
FIG. 2 illustrates a perspective view of the tray without the lid of FIG. 1.

The tray includes an interior 26 for storage and/or reprocessing of the endoscope, as shown in FIG. 2. The interior is defined by an inner surface 28 that forms a base 30 and surrounding sidewalls 32 upstanding therefrom. The sidewalls can be continuous and monolithic with the base of the tray. The sidewalls can include openings or handles 34 to assist a user in moving and/or carrying the tray. In some embodiments, a portion of the opening or handle can be formed from a side 35 of the lid, as shown in FIG. 1.

Figure 3:
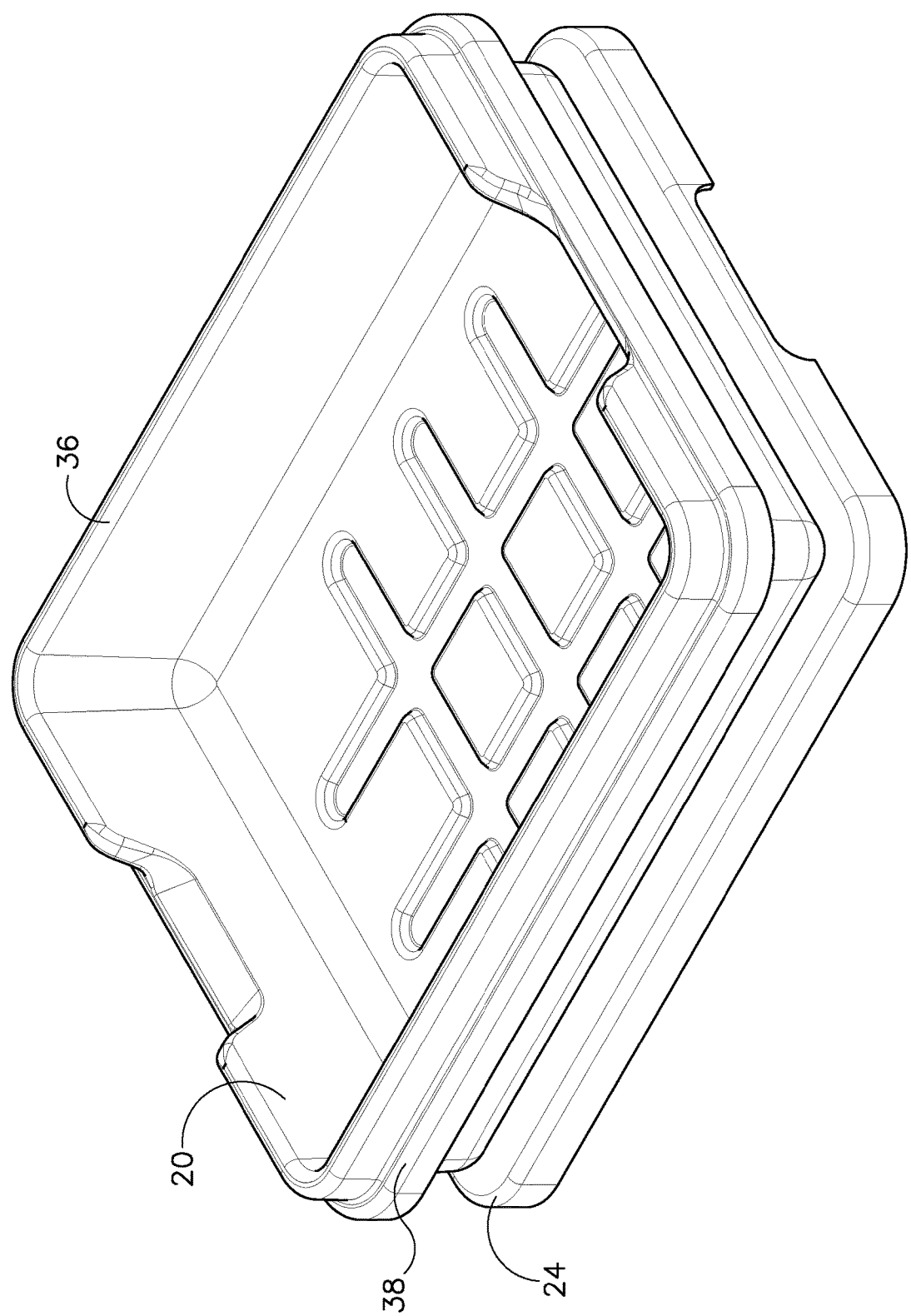
FIG. 3 illustrates a perspective view of the tray with the shaped recess and projections of the lid mating with the recesses and the shaped projection of the bottom exterior surface of the tray. The recess and projections of the lid are not shown.
Figure 4:
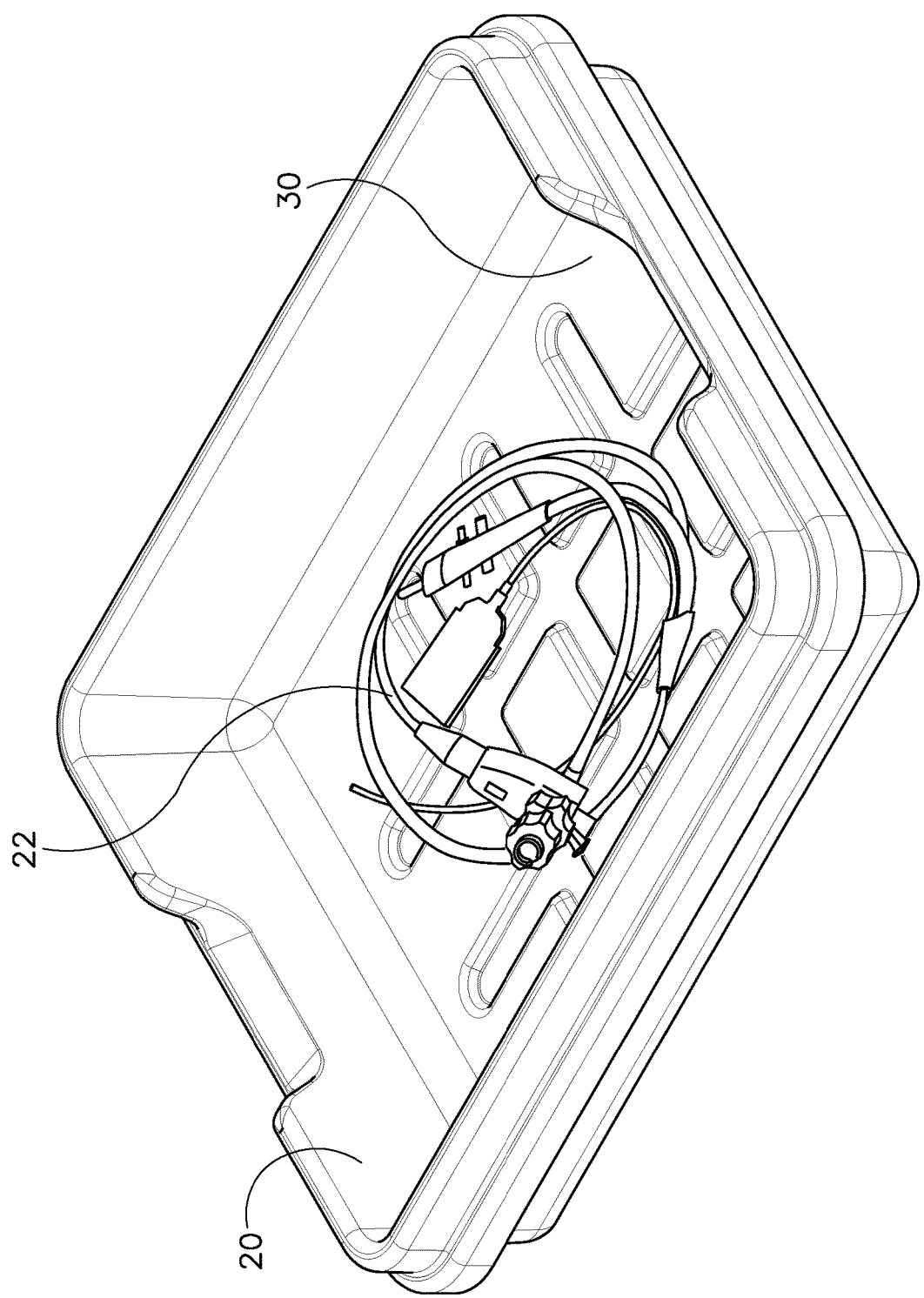
FIG. 4 illustrates a perspective view of the tray with an endoscope disposed within the interior of the tray.

As shown in FIG. 3, the tray can include a rim 36 and a peripheral lip 38 disposed at least partially around the surrounding sidewalls and extending outwardly therefrom. The rim and/or the lip are configured for engagement with a perimeter 48 of the lid so that the lid covers the tray, as shown in FIG. 1. The lid can have a friction fit engagement with the tray when covering the tray. In some embodiments, the lid can self-seal with the rim of the tray by a natural vacuum created when the lid is mated with the tray.

The tray includes a bottom exterior surface 40, as shown in FIG. 6. The bottom exterior surface is configured to mate with the lid when the tray is stacked on top of the lid. The bottom exterior surface of the tray includes one or a plurality of recesses 41 and/or projections 42 that are configured to mate with one or a plurality of recesses 43 and/or projections 44 formed from an exterior surface 46 of the lid, as shown in FIGS. 5-8. It is to be understood that one or a plurality of projections defined from the tray will mate with corresponding one or a plurality of recesses defined from the lid and one or a plurality of recesses defined from the tray will mate with corresponding one or a plurality projections defined from the lid.

Mating engagement of the recesses and/or projections of the tray and the lid reduces lateral side to side movement of the tray when the bottom exterior surface of the tray is stacked on the exterior surface of the lid. The mating engagement of the recesses and/or projections of the tray and the lid creates a locked engagement, thereby allowing a user to lift one or multiple trays with lids together as a single unit so that the trays and lids can be moved from one location to another location without detaching. The mating engagement described above also reduces the probability of an endoscope being dropped or contaminated during transport. It is to be understood that the lid can mate with the recesses and/or projections of the tray when the tray is uncovered, as shown in FIG. 3.

The recesses and/or projections of the tray, in some embodiments, are configured to provide increased strength to the bottom exterior surface of the tray and the recesses and/or projections of the lid provide increased strength to the lid to help prevent deformation during reprocessing such as a cart washing cycle at an elevated temperature.

The recesses and/or projections of the bottom exterior surface of the tray and the lid can be friction fittings that when mated, reduce lateral side to side movement of the tray, as described above and shown by the arrows in FIG. 7. The recesses and/or projections can also have a male/female engagement, tab/slot engagement, snap engagement, and/or compressive engagement. The bottom exterior surface of the tray and/or the exterior surface of the lid can have 1 to about 100 recesses and/or projections. In some embodiments, the bottom exterior surface of the tray and/or the exterior surface of the lid can have 1 to about 80, 1 to about 75, 1 to about 60, 1 to about 50, 1 to about 40, 1 to about 25, 1 to about 20, 1 to about 15, 1 to about 10, 1 to about 5 or 1 to about 2 recesses and/or projections. The tray and/or the lid can have 1, 2, 3, 4, 5, 6, 7, 8, 9, 10, 15, 20, 25, 30, 35, 40, 45, 50, 55, 60, 65, 70, 75, 80, 85, 90, 95 to about 100 recesses and/or projections.

Figure 8:
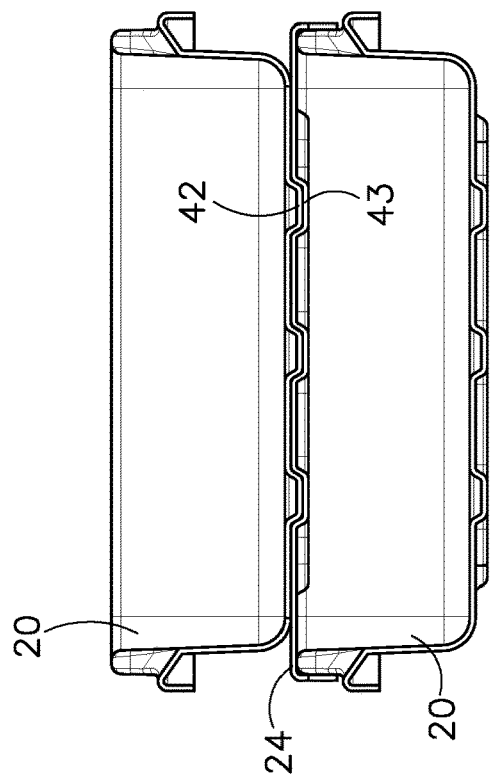
FIG. 8 illustrates a side view of the stacked configuration of FIG. 5.
Figure 7:
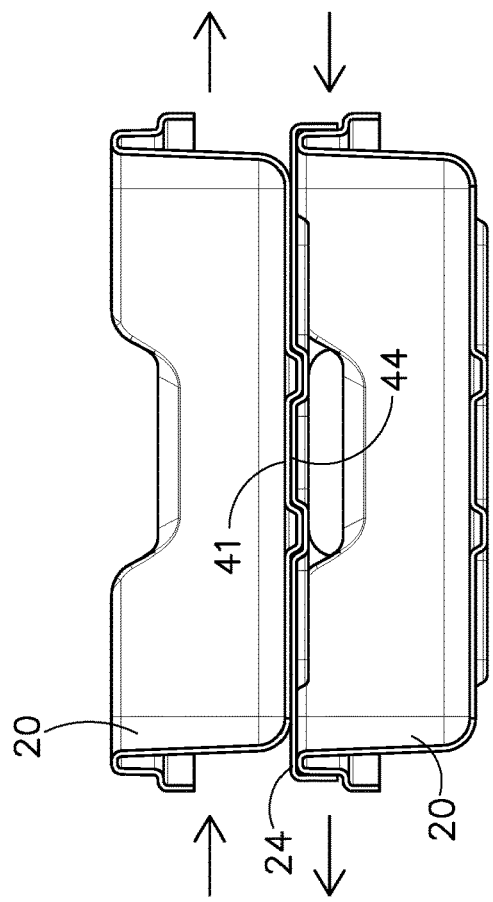
FIG. 7 illustrates a front view of the stacked configuration of FIG. 5. The arrows show that mating engagement of the recesses and/or projections of the tray and the lid reduce lateral side to side movement of the tray that can damage an endoscope stored within the tray.
Figure 9:
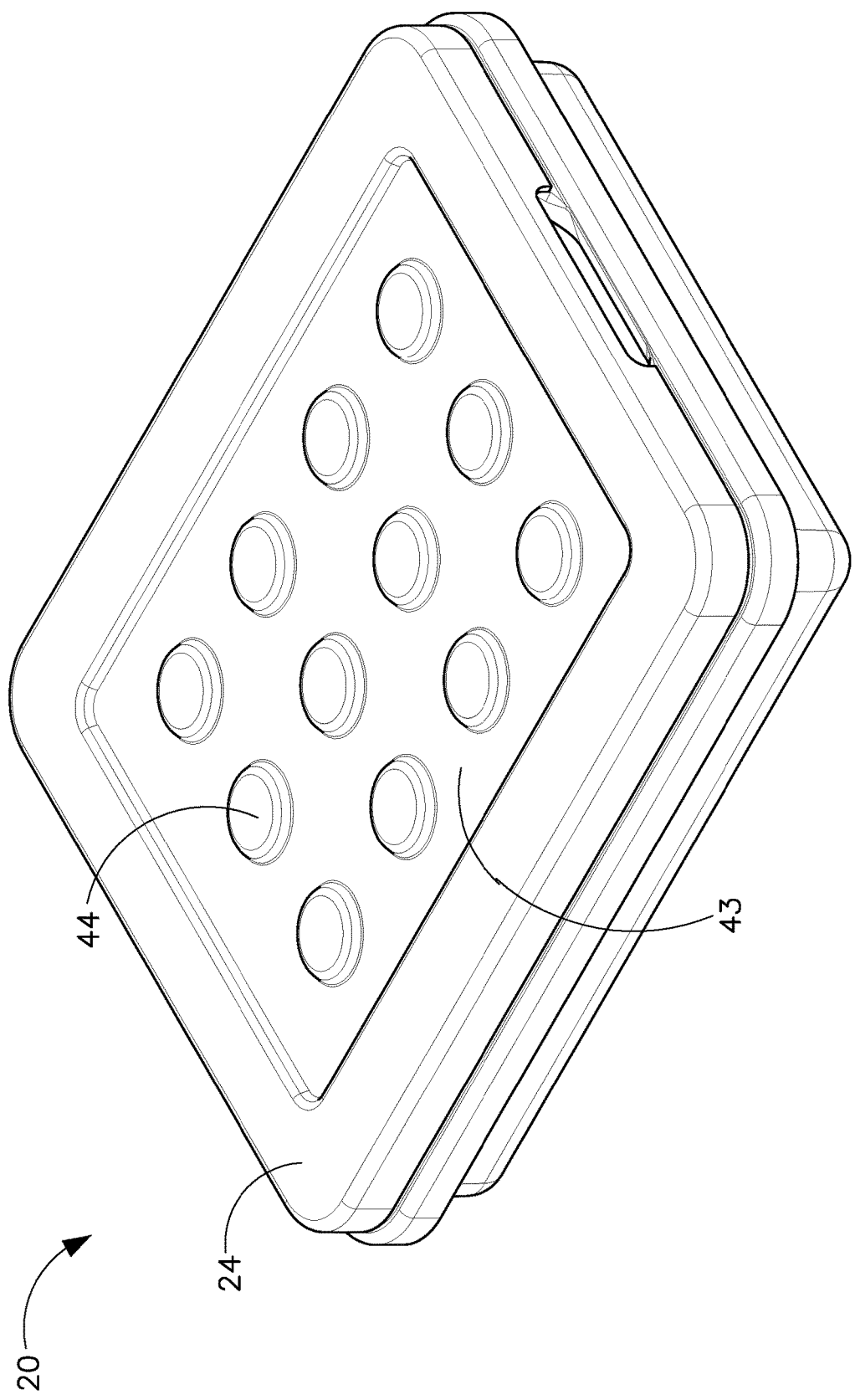
FIG. 9 illustrates a perspective view of an embodiment of the tray of FIG. 1 where the tray has a pattern shaped projection and a plurality of circular shaped recesses (not shown) and the lid has a pattern shaped recess and a plurality of circular shaped projections.

The recesses and/or projections can be arranged in a pattern shape and/or can include geometric shapes, as shown in FIGS. 1-21. For example, as shown in FIGS. 1-8, the tray includes a pattern shaped projection and square shaped recesses disposed within a center of the tray and the lid includes a corresponding pattern shaped recess and square shaped projections disposed within a center of the lid. The pattern shaped projection of the tray will mate with the corresponding pattern shaped recess of the lid and the square shaped recesses of the tray will mate with the corresponding square shaped projections of the lid to matingly lock the tray with the lid, as shown in FIG. 6-8.

Figure 14:
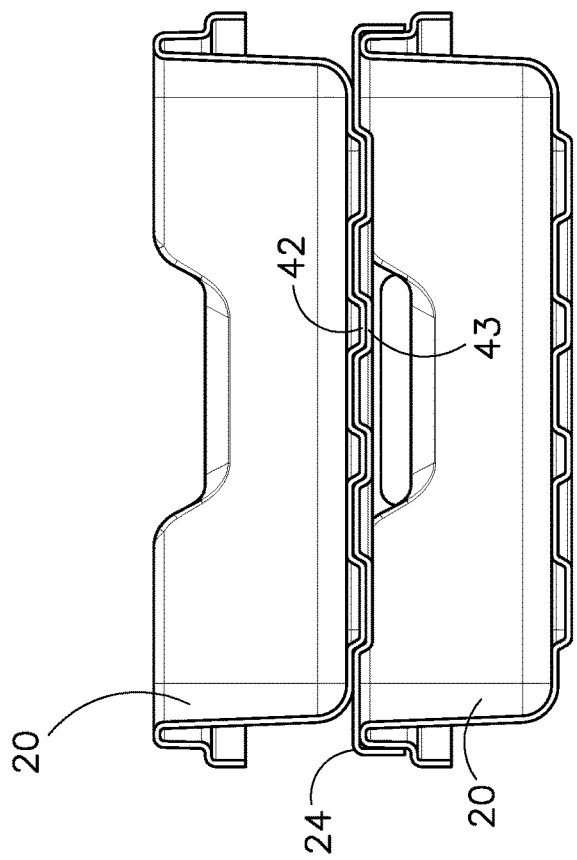
FIG. 14 illustrates a side view of the stacked configuration of FIG. 9.
Figure 13:
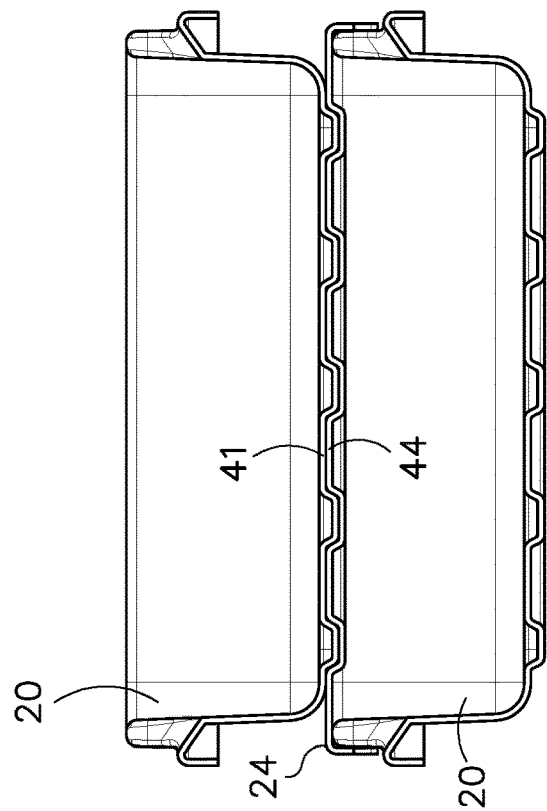
FIG. 13 illustrates a front view of the stacked configuration of FIG. 9.

As shown in FIGS. 9-14, the tray can include a pattern shaped projection and circular shaped recesses and the lid includes a pattern shaped recess and circular shaped projections. The pattern shaped projection of the tray will mate with the corresponding pattern shaped recess of the lid and the circular shaped recesses of the tray will mate with the corresponding circular shaped projections of the lid to matingly lock the tray with the lid, as shown in FIG. 12-14.

Figure 15:
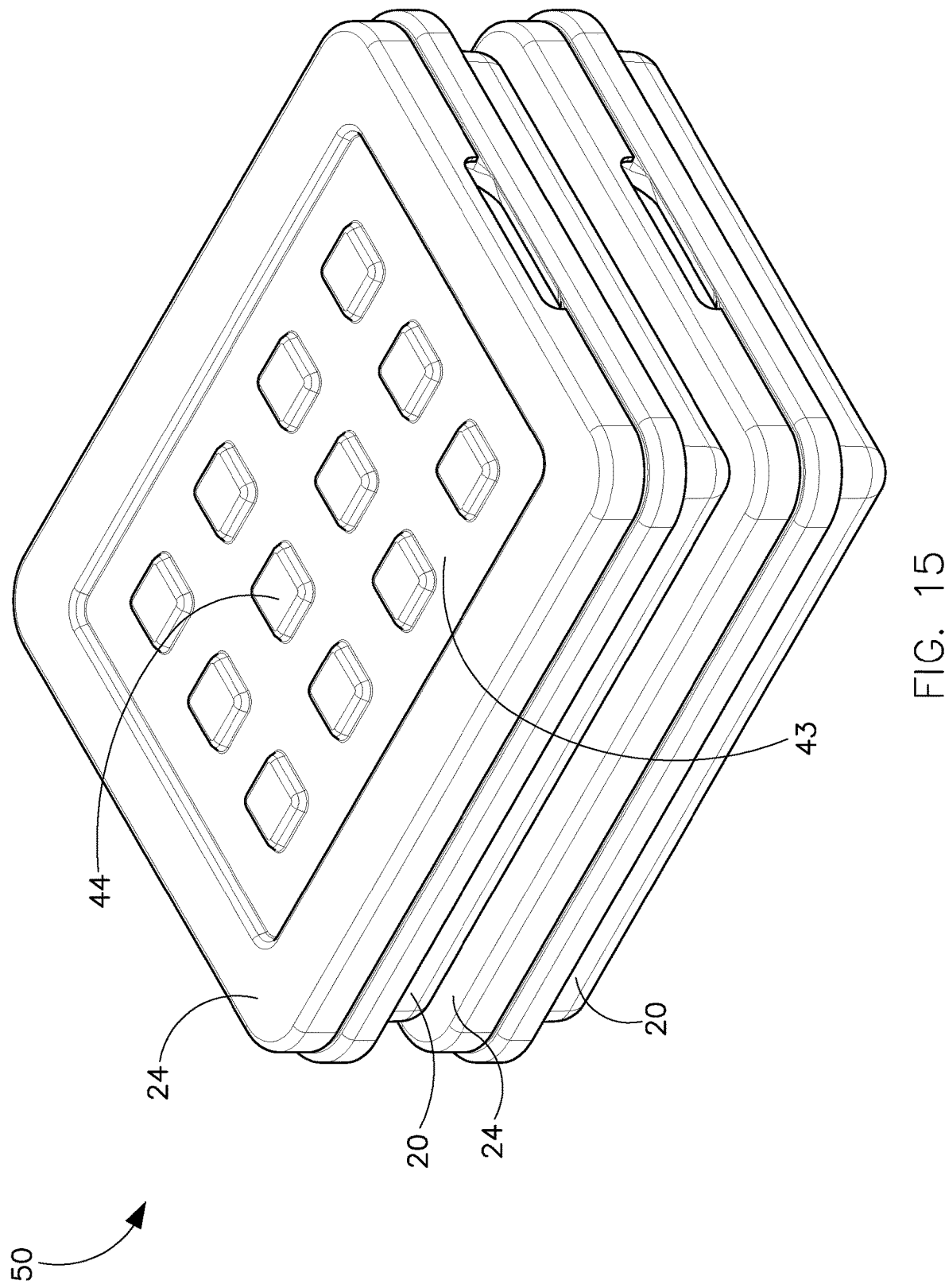
FIG. 15 illustrates a perspective view of an embodiment of the tray of FIG. 1 where the tray has a pattern shaped projection and a plurality of rectangular shaped recesses (not shown) and the lid has a pattern shaped recess and a plurality of rectangular shaped projections. The tray and the lid are engaged with a second tray in a stacked configuration.

As shown in FIG. 15, the tray can include a pattern shaped projection with square and rectangular shaped recesses and the lid can include a pattern shaped recess with square and rectangular shaped projections. The pattern shaped projection of the tray will mate with the corresponding pattern shaped recess of the lid and the square and rectangular shaped recesses of the tray will engage with the corresponding square and rectangular shaped projections of the lid to mate, locking the tray with the lid.

Figure 16:
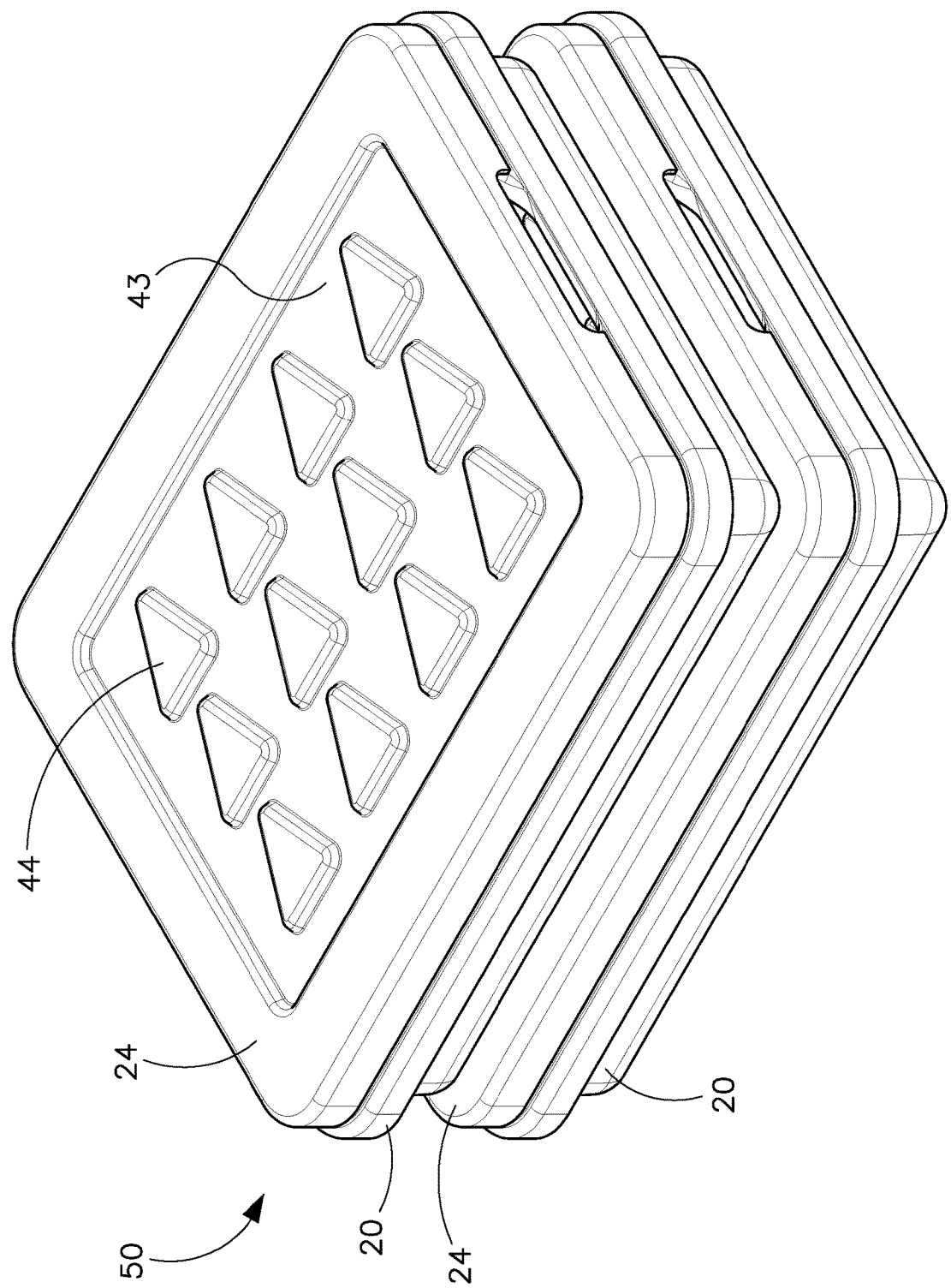
FIG. 16 illustrates a perspective view of an embodiment of the tray of FIG. 1 where the tray has a pattern shaped projection and a plurality of triangular shaped recesses (not shown) and the lid has a pattern shaped recess and a plurality of triangular shaped projections. The tray and the lid are engaged with a second tray in a stacked configuration.

As shown in FIG. 16, the tray can include a pattern shaped projection and triangular shaped recesses and the lid can include a pattern shaped recess and triangular shaped projections. The pattern shaped projection of the tray will mate with the corresponding pattern shaped recess of the lid and the triangular shaped recesses of the tray will engage with the corresponding triangular shaped projections of the lid to mate, locking the tray with the lid.

Figure 17:
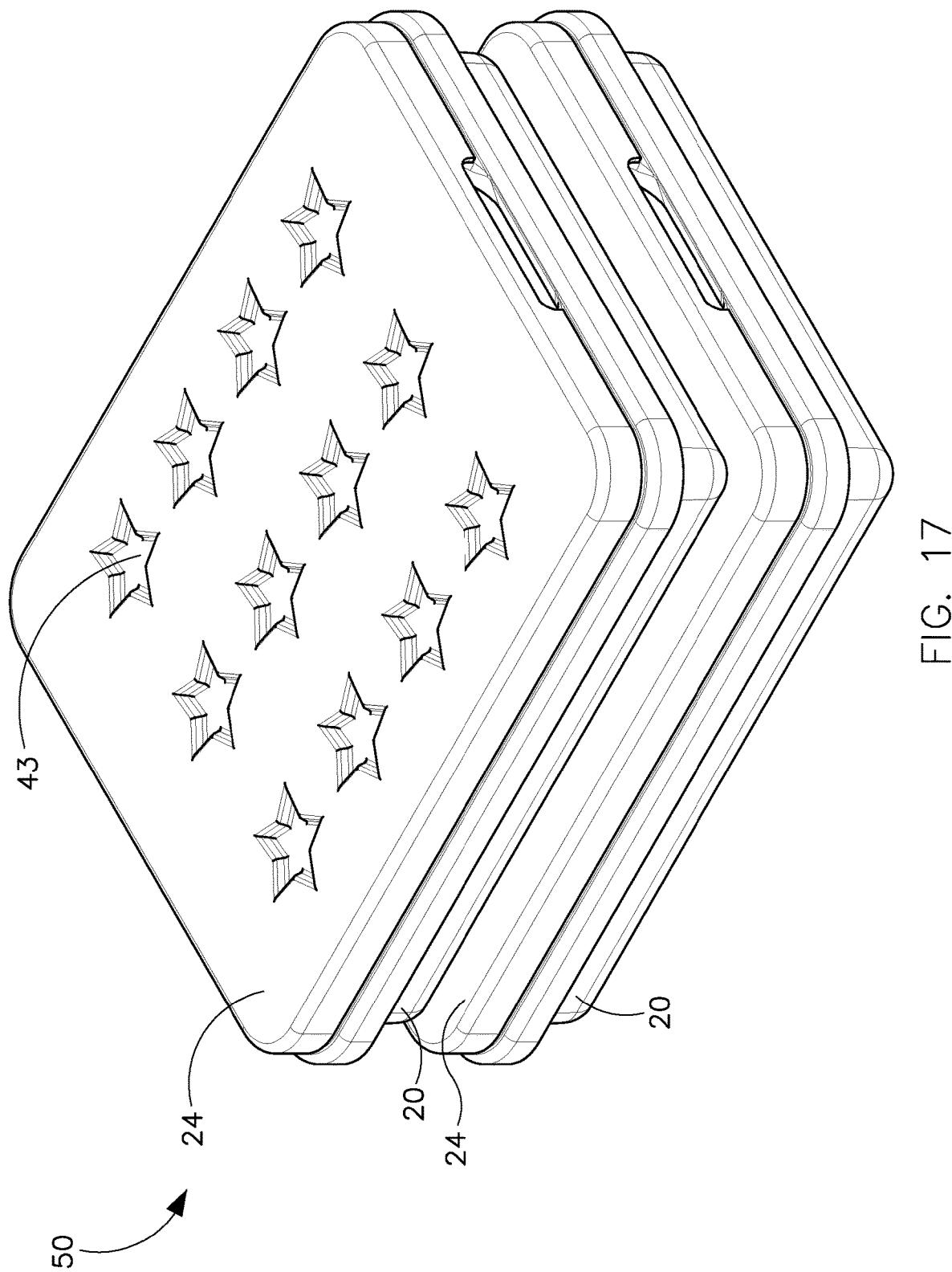
FIG. 17 illustrates a perspective view of an embodiment of the tray of FIG. 16 where the tray has a plurality of star shaped projections (not shown) and the lid has a plurality of star shaped recesses. The tray and the lid are engaged with a second tray in a stacked configuration.
Figure 18:
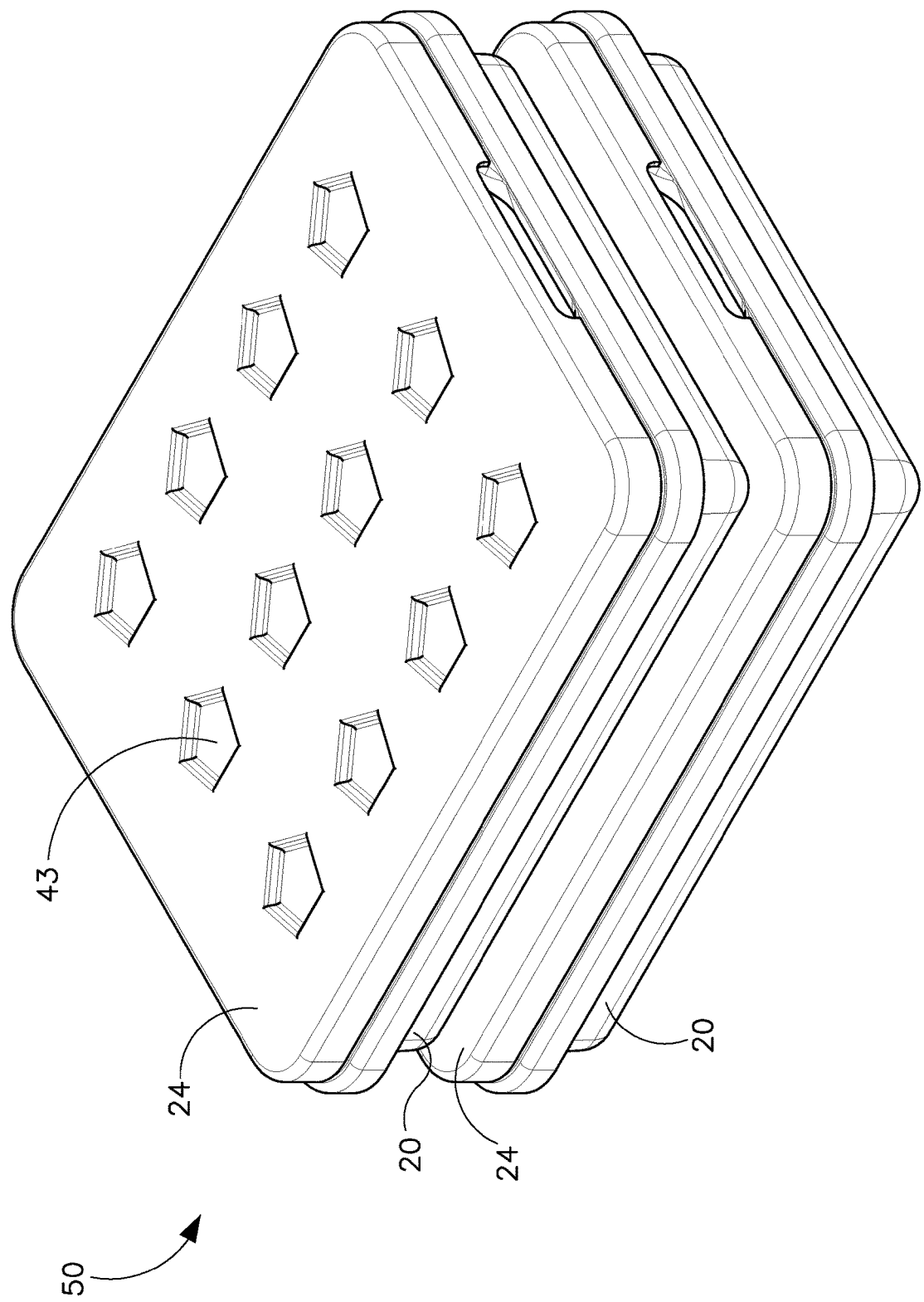
FIG. 18 illustrates a perspective view of an embodiment of the tray of FIG. 16 where the tray has a plurality of pentagonal shaped projections (not shown) and the lid has a plurality of pentagonal shaped recesses. The tray and the lid are engaged with a second tray in a stacked configuration.
Figure 19:
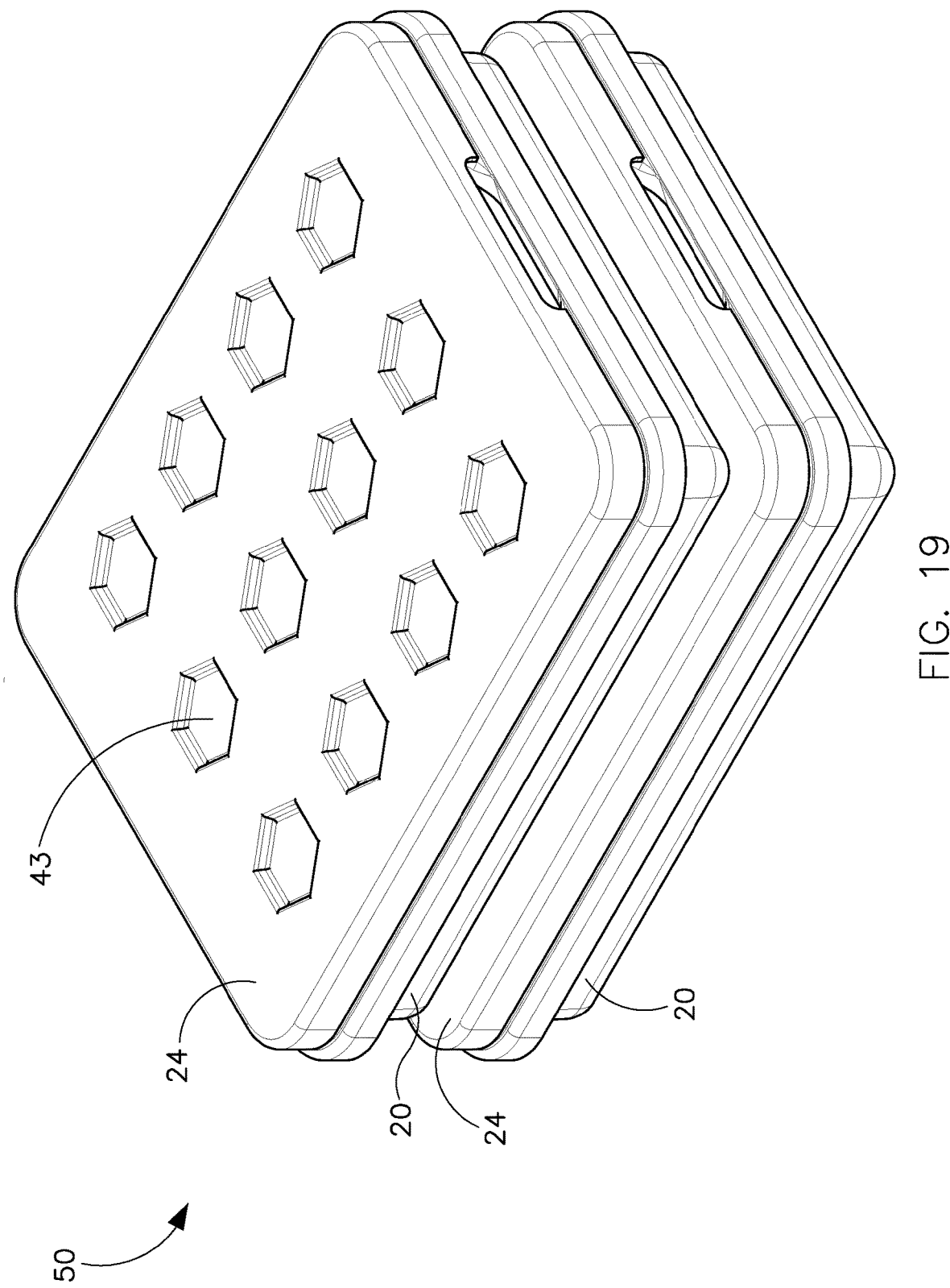
FIG. 19 illustrates a perspective view of an embodiment of the tray of FIG. 16 where the tray has a plurality of hexagonal shaped projections (not shown) and the lid has a plurality of hexagonal shaped recesses. The tray and the lid are engaged with a second tray in a stacked configuration.
Figure 20:
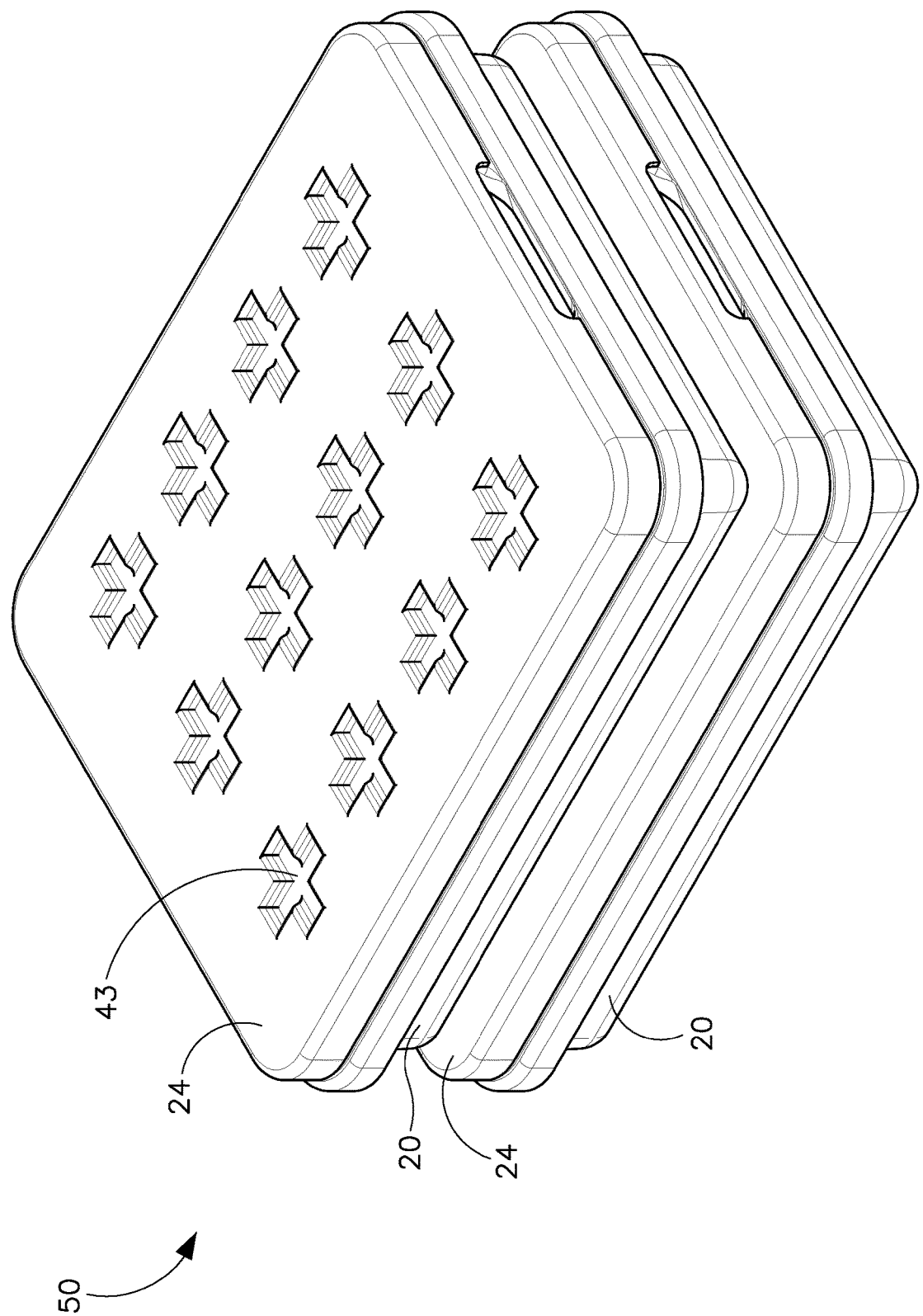
FIG. 20 illustrates a perspective view of an embodiment of the tray of FIG. 16 where the tray has a plurality of cross shaped projections (not shown) and the lid has a plurality of cross shaped recesses. The tray and the lid are engaged with a second tray in a stacked configuration.
Figure 21:
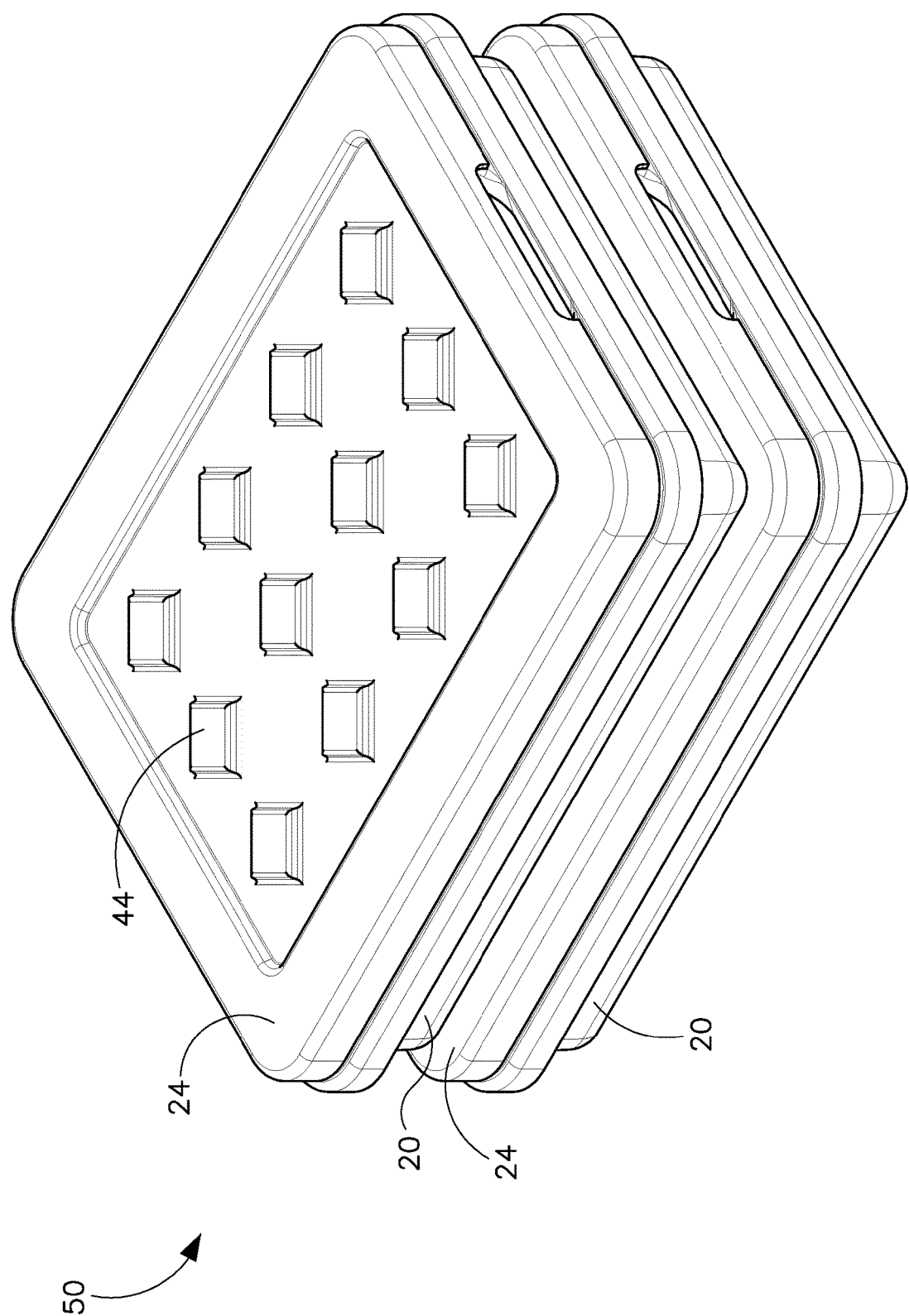
FIG. 21 illustrates a perspective view of an embodiment of the tray of FIG. 16 where the tray has a plurality of diamond shaped recesses (not shown) and the lid has a plurality of diamond shaped projections. The tray and the lid are engaged with a second tray in a stacked configuration.

The tray can include star shaped projections and the lid can include star shaped recesses, as shown in FIG. 17. The tray can include pentagonal shaped projections and the lid can include pentagonal shaped recesses, as shown in FIG. 18. The tray can include hexagonal shaped projections and the lid can include hexagonal shaped recesses, as shown in FIG. 19. The tray can include cross shaped projections and the lid can include cross shaped recesses, as shown in FIG. 20. The tray can include diamond shaped recesses and the lid can include diamond shaped projections, as shown in FIG. 21. It is to be understood that the shaped configurations of the recesses and projections on the tray and the lid of FIGS. 15-21 can be the reverse of what is described above. For example, rather than the tray having star shaped projections and the lid having star shaped recesses, the tray can have star shaped recesses and the lid can have star shaped projections.

It is contemplated that the recesses and/or projections can be any shape such as geometric or otherwise, and can be a mix of shapes disposed on a single tray and/or lid. Shapes include, but are not limited to a nonagon, octagon, heptagon, hexagon, triangle, scalene triangle, right triangle, parallelogram, rhombus, square, pentagon, circle, oval, heart, cross, arrow, cube, cylinder, star, crescent, a wavy line, semicircular, ring, quatrefoil shaped or a combination thereof. The shapes can be regular, irregular and/or freeform.

It is further contemplated that the tray and the lid can each include both recesses and projections or recesses or projections. The recesses and/or projections can be oriented in a discrete or a random pattern on the bottom exterior surface of the tray and/or the exterior surface of the lid. The recesses and/or projections can cover the entire bottom exterior surface of the tray or only portions of the bottom exterior surface of the tray. Similarly, the recesses and/or projections can cover the entire exterior surface of the lid or only portions of the exterior surface of the lid.

The recesses and/or projections can have various surfaces configurations such as, smooth, rough, arcuate, undulating, porous, semi-porous, dimpled, knurled, polished and/or textured. The recesses and/or projections can also be a certain size, such as, for example, from about 1 millimeter (mm) to about 4 inches in length, width, thickness and/or height. It is contemplated that the recesses and/or projections can be from about 1, 5, 10, 15, 20, 25 mm, 1, 2, 3 to about 4 inches in length, width, thickness and/or height.

The recesses and/or the projections of the tray can be spaced apart a certain distance from each other on the bottom exterior surface of the tray. For example, each recess and/or projection can be 1 mm to about 10 inches from each other. In some embodiments, each recess and/or projection can be 1, 2, 3, 4, 5, 6, 7, 8, 9, 10, 11, 12, 13, 14, 15, 16, 17, 18, 19, 20, 21, 22, 23, 24, 25 mm, 1, 2, 3, 4, 5, 6, 7, 8, 9 and/or 10 inches from each other on the bottom exterior surface of the tray. In a similar manner, the recesses and/or projections of the lid can be spaced apart a certain distance from each other on the exterior surface of the lid. For example, each recess and/or projection can be 1 mm to about 10 inches from each other, as described above. It is to be understood that the distance between each recess and/or projection of the tray will be equal to and correspond to the distance between the recesses and/or projections located on the lid so that the tray and lid matingly engage.

It is contemplated that more than one tray and one lid can be implemented. For example, 1 to about 10 trays and 1 to about 10 lids can be used and stacked together. In some embodiments, 1, 2, 3, 4, 5, 6, 7, 8, 9 to about 10 trays and 1, 2, 3, 4, 5, 6, 7, 8, 9 to about 10 lids can be stacked together in a mating engagement, which locks the trays with the lids.

The recesses and/or projections of the tray and/or the lid can be vacuum formed or injection molded. The recesses and/or projections can also be monolithic to the exterior surfaces of the tray and lid or can be in an over-molded configuration. It is to be understood that in some embodiments, the mold or shape of the recesses and/or projections will be seen within the interior of the tray molded into the base, as shown in FIG. 2.

Once the trays and lids of the present application are assembled and stacked, side to side or lateral movement will be eliminated or reduced, which reduces damage to the endoscope stored within the tray during transport. The stacked trays can more easily be transported by hand or in a cart or cabinet to the desired area as there is more stability to the stacked trays.

Because the trays and lids of the present application are more stable when stacked, the risk of one or more trays falling is reduced, which reduces further damage to the endoscope during transport. The more stable storage and transport of endoscopes in the trays also reduces or prevents the chance of an endoscope falling out of the tray and being misplaced in a different tray, which may lead to difficulties in tracking the endoscope before or after use. Tracking of the endoscope is essential for quality assurance purposes and for patient tracing to avoid cross-contamination among patients.

The tray can be made from a material such as, for example, a polymeric material. The polymeric material can be thermoplastic and/or is a polycarbonate. For example, the tray can be fabricated from materials such as machined or injection molded thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, polyphenylene, polychloropene, polyamide, polyetherimide, polyethylene, epoxy, partially resorbable materials, totally resorbable materials, polyglycolide, polytyrosine carbonate, polycaprolactone, silicone based rubber, liquid silicone rubber, High Consistency Rubber, silicon, TPE, Polypropylene, Polycarbonate, ABS or any combination thereof. The tray can also be made from steel, aluminum, paper, bamboo, cork, glass, hemp or any combination thereof.

In some embodiments, the tray can have a certain length, width and height. In some embodiments, the length of the tray can be from about 16 to about 34 inches, the width can be from about 12 to about 24 inches and the height can be from about 3 to about 8 inches. In some embodiments, the length of the tray can be from about 16, 18, 20, 22, 24, 26, 28, 30, 32 to about 34 inches, the width of the tray can be from about 12, 14, 16, 18, 20, 22 to about 24 inches, and the height of the tray can be from about 3, 4, 5, 6, 7 to about 8 inches.

The components of the tray, individually or collectively, may also be fabricated from a heterogeneous material such as a combination of two or more of the above-described materials. The tray as described herein may be constructed of a suitable biocompatible material to impart various desirable characteristics, such as rigidity, and resilience.

Components of the tray can also be made from a suitable material such as for example, polyurethane, polyurea, polyether (amide), PEBA, thermoplastic elastomeric olefin, copolyester, styrenic thermoplastic elastomer, carbon fiber, glass fiber, ceramics, methacrylates, poly (N-isopropylacrylamide), plastic (e.g., polycarbonates), ABS, MABS, or the like or combinations thereof.

Storage System

Referring to FIGS. 1-31, a stackable tray system 50 for storage of an endoscope(s) is provided. The system comprises a tray 20, endoscope 22 and lid 24, as described above. For example, as shown in FIGS. 1, 9 and 15-21, the system can include a first tray 20 having a first lid 24 configured to cover the first tray, and a second tray 20 having a second lid 24 configured to cover the second tray. The recess and/or projection of the exterior surface of the first lid of the first tray is configured to mate with the recess and/or projection of the bottom exterior surface of the second tray when the first tray and the second tray are stacked together to reduce lateral side to side movement of the first tray and the second tray. It is to be understood that the first lid and the second lid are interchangeable or the first lid and the second lid are not interchangeable. As described above, one or more trays and lids can be implemented with the system such as 1 to about 10 trays and 1 to about 10 lids.

Figure 22:
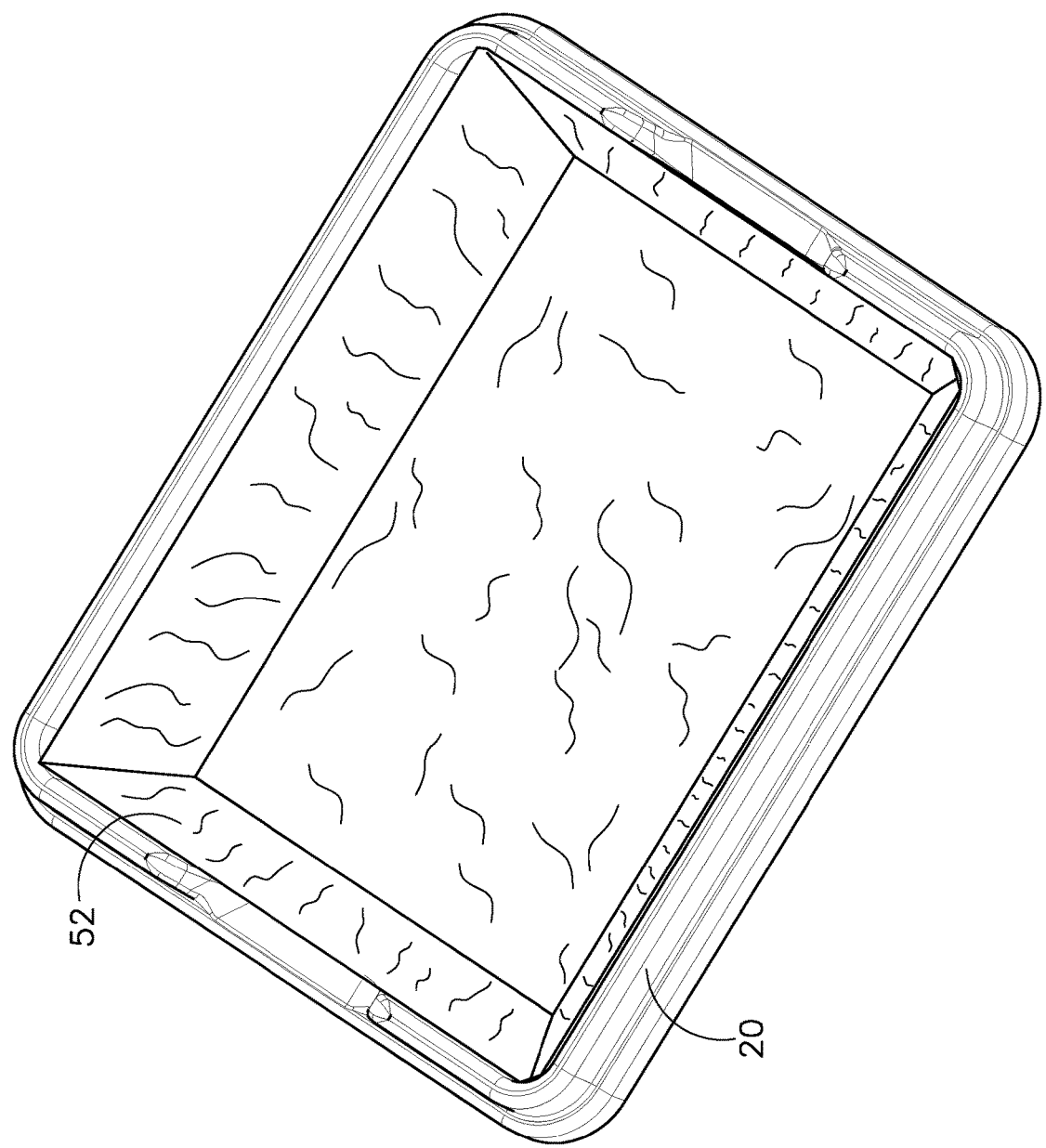
FIG. 22 illustrates a perspective view of a disposable liner disposed within an interior of the tray.
Figure 23:
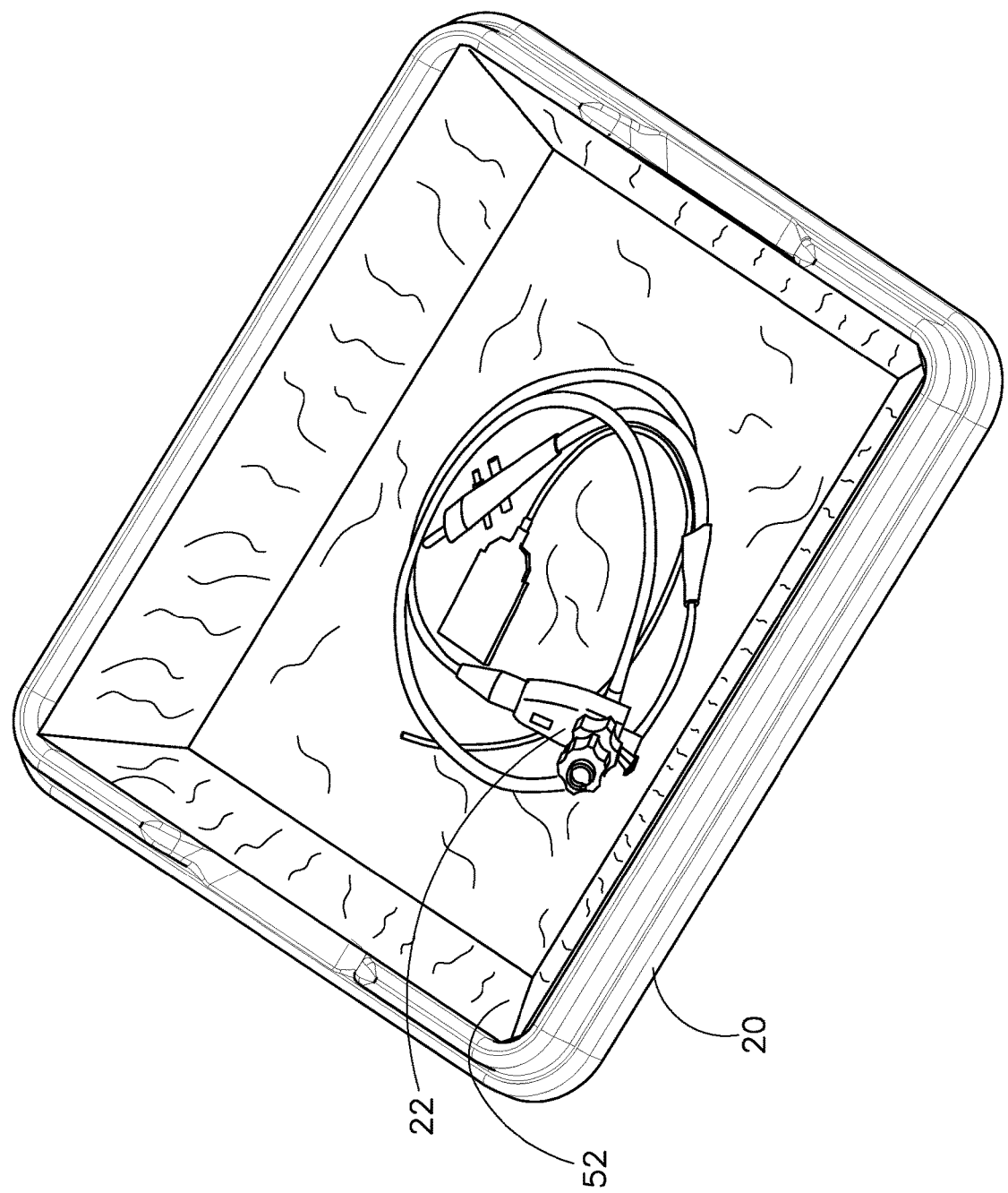
FIG. 23 illustrates a perspective view of the disposable liner of FIG. 22 having an endoscope placed on top of the disposable liner.

The system can include a liner 52, as shown in FIGS. 22-23. The liner is configured to engage with the interior of the tray and the endoscope, as shown in FIG. 23. The liner can be configured to engage contours of the interior and rim of the tray. In some embodiments, the liner is similar to the liner found and described in U.S. Pat. No. 6,749,063, assigned to Cantel (UK) Limited. This patent herein is incorporated by reference. The liner can be disposable and can be substantially impermeable to fluids.

The tray interior and portions of the exterior of the tray can be engaged by the liner. The liner can be made of a flexibly deformable material substantially impermeable to fluids. The disposable liner can contact the bottom surface of the tray and at least partially encloses the reprocessed endoscope. In some embodiments, the liner is a disposable single use liner that may be sterile or unsterile.

The disposable liner can be configured to temporarily line the entirety of the interior of the tray and prevent the endoscope from having direct contact with the interior of the tray. In some embodiments, the liner prevents moisture from the reprocessed endoscope from contacting the tray and when the tray is used repeatedly, it prevents or reduces contamination from one endoscope to the next endoscope. In some embodiments, the disposable liner can be in a sheet or bag configuration.

Figure 24:
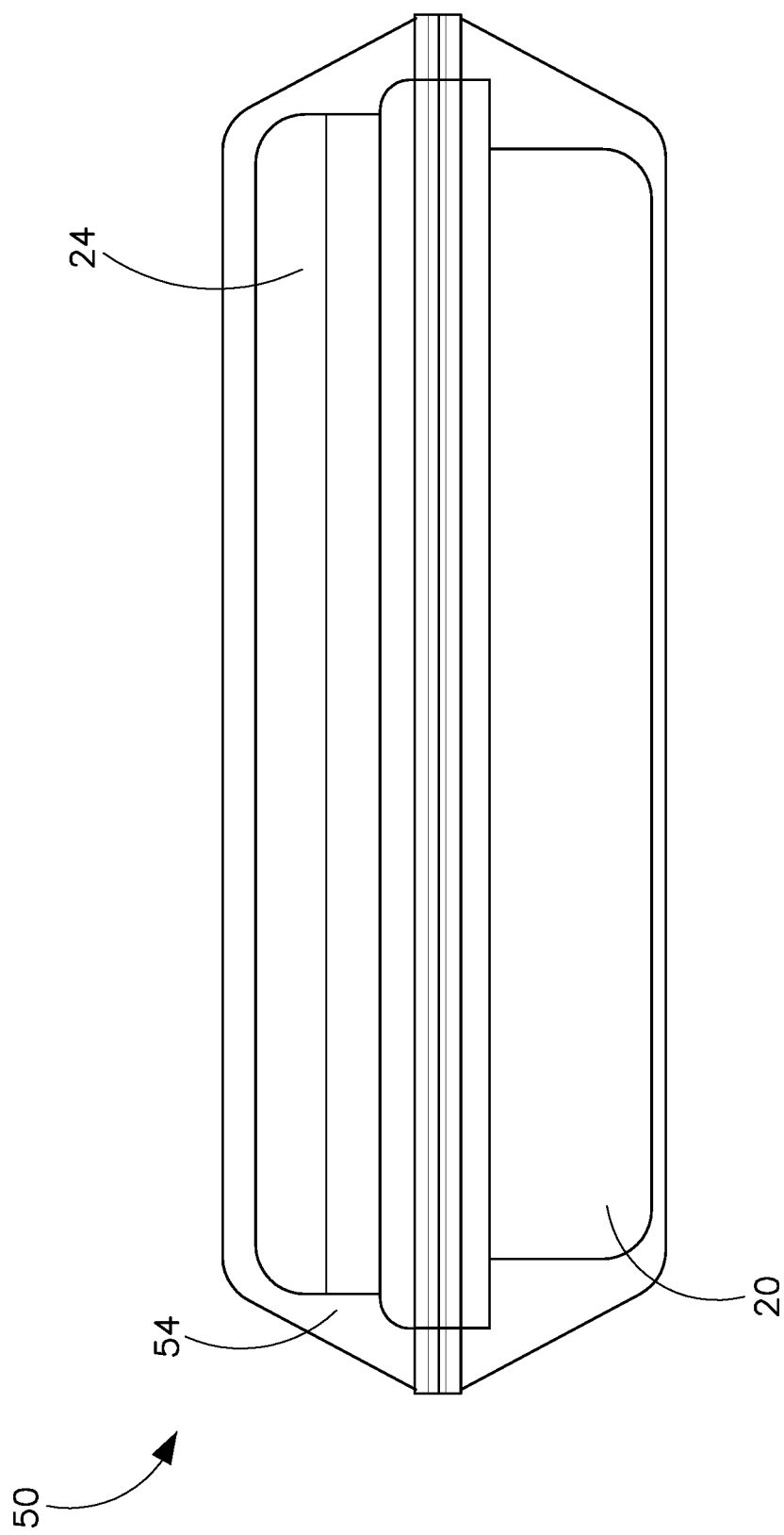
FIG. 24 illustrates a side view of the tray and the lid of FIG. 1 disposed within a flexible cover so that the flexible cover encloses both the tray and lid.
Figure 25:
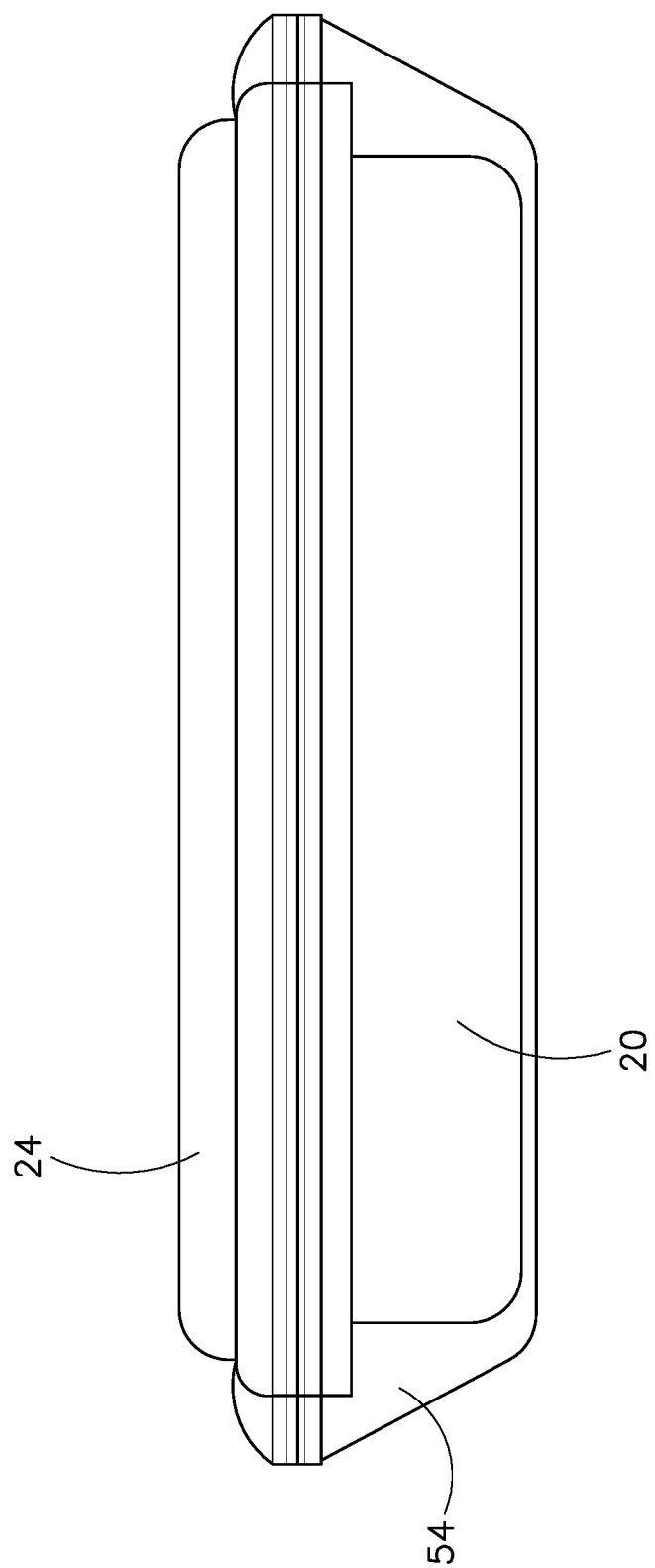
FIG. 25 illustrates a side view of the tray and the lid of FIG. 1, and a flexible cover. The flexible cover encloses the tray and the lid is disposed over the cover.

The tray whether it is lined or not lined can be temporarily covered with a disposable cover 54, as shown in FIGS. 24-30. The cover can be a puncture resistant flexible cover configured to enclose or partially enclose the tray when it is covered or uncovered with the lid. As shown in FIG. 24, the cover can enclose the tray and the lid, or the cover can enclose the tray and the lid can be disposed on top of the cover to close the tray, as shown in FIG. 25.

The disposable cover can at least partially enclose or entirely enclose the reprocessed endoscope and the tray. The cover can be a disposable single use cover that may be sterile or unsterile. In some embodiments, the cover can be similar to the cover found and described in U.S. Pat. No. 6,749,063, assigned to Cantel (UK) Limited. This patent is herein incorporated by reference.

The cover can include a flexibly deformable sheet material substantially impermeable to fluids. The flexibly deformable sheet material can be configured to be temporarily secured to the tray so as to cover at least the interior of the tray. The cover can also engage with the rim and/or the lip of the tray to temporarily secure the cover to the tray.

Figure 27:
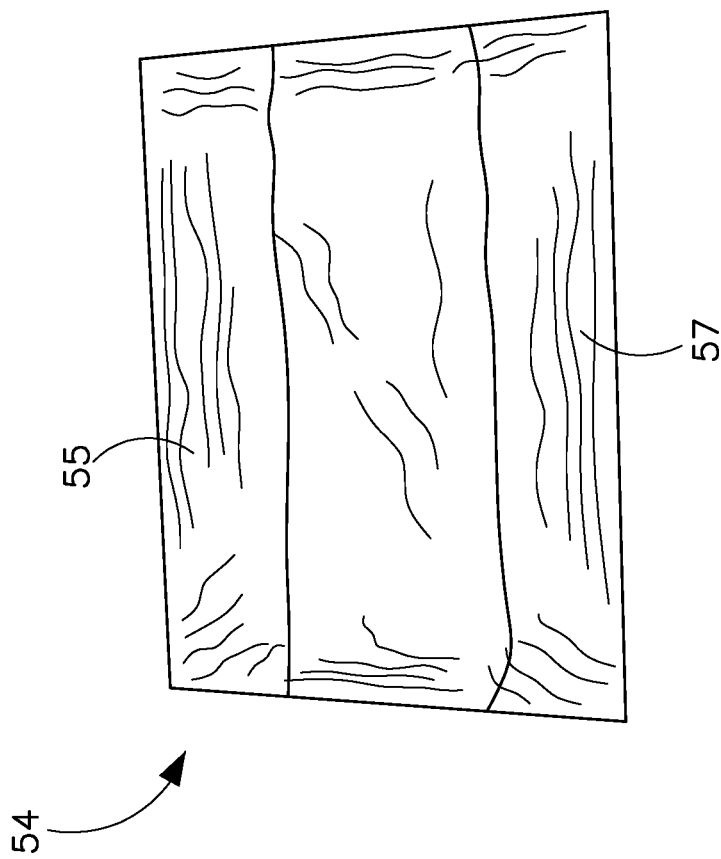
FIG. 27 illustrates a bottom perspective view of the flexible cover of FIG. 26.
Figure 26:
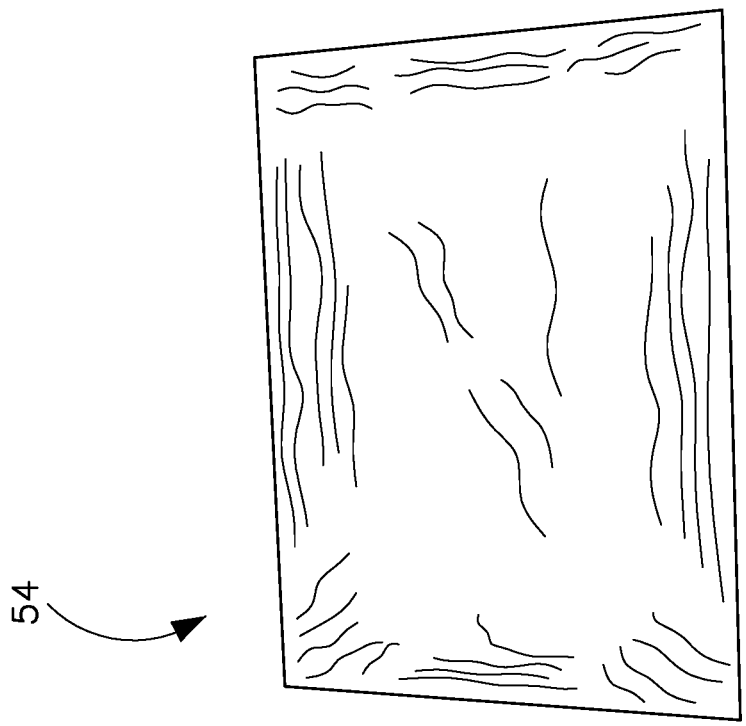
FIG. 26 illustrates a top perspective view of a flexible cover in a sheet configuration.

The cover can be in a sheet (FIGS. 26-27) or a bag/pouch configuration (FIGS. 29-30). When the cover is in a sheet configuration, as shown in FIGS. 26-27, a first fold 55 and a second fold 57 are configured to be temporarily secured to the rim of the tray. The folds can be secured to the rim of the tray via tension or an elastic band. In some embodiments, the folds can be secured to the rim of the tray by a removable adhesive.

As shown in FIGS. 29-30, when the cover is in a bag/pouch configuration, the cover can be a reversible pouch. The reversable bag/pouch is configured to entirely enclose the tray and the lid, or entirely enclose the tray and the lid can be disposed on top of the cover to close the tray. The reversible bag/pouch can have a clean/green colored side 56 and a biohazard/red side 58. The clean/green side can have indicia 60 in the form of a word, words and/or symbols. For example, the indicia can be the word "CLEAN". In some embodiments, the biohazard/red side can have indicia 62 in the form of a word, words and/or symbols. For example, the indicia can be the word "BIOHAZARD". Alternatively, the indicia can be the word "CONTAMINATED". When the tray is inserted/engaged into a cart, as described below, and the clean/green side is facing upward, this can indicate to a user that the endoscope is clean and ready for use. When the tray is inserted/engaged into the cart and the biohazard/red side is facing upward, this can indicate to a user that the endoscope is contaminated, should not be used and that the endoscope needs to be reprocessed. In some embodiments, the reversible bag/pouch can have a clear/transparent viewing window 64 in the center of each side of the bag/pouch. The reversible bag/pouch can also be sealed by a zipper 65 or adhesive seal to enclose the tray.

Figure 28:
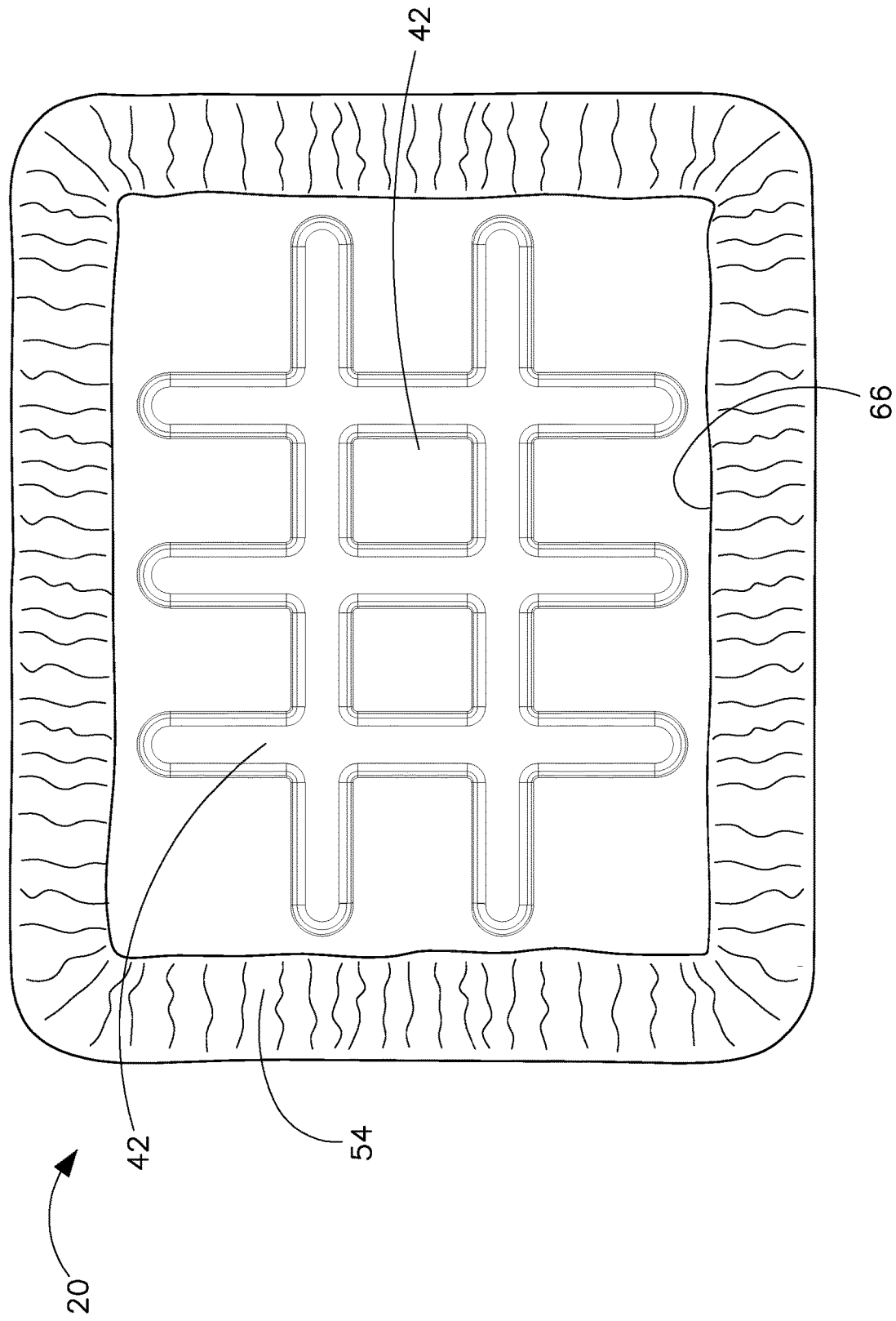
FIG. 28 illustrates a bottom perspective view of a flexible cover engaged with the bottom of the tray to enclose the tray.

In some embodiments, the cover engages and partially encloses the tray with an elastic portion 66, as shown in FIG. 28. The sheet or bag configuration can have a rectangular shape to correspond with the shape of the tray but other cover shapes are contemplated depending on tray shape. These shapes include oval, square, circular or the like. In some embodiments, the cover can be temporarily secured to the rim of the tray, and/or the bottom of the tray.

The cover can be manufactured in different colors such as in a green or a clear color to indicate that the endoscope is clean and ready for use. A red color, in some embodiments, could indicate that the tray should not be used and the endoscope should be cleaned. Alternative colors can be selected such as blue, pink, yellow, orange, brown or black to indicate the status of the endoscope. The cover can be reversible and a different color can be used on the inner surface than on the outer surface of the cover.

Figure 31:
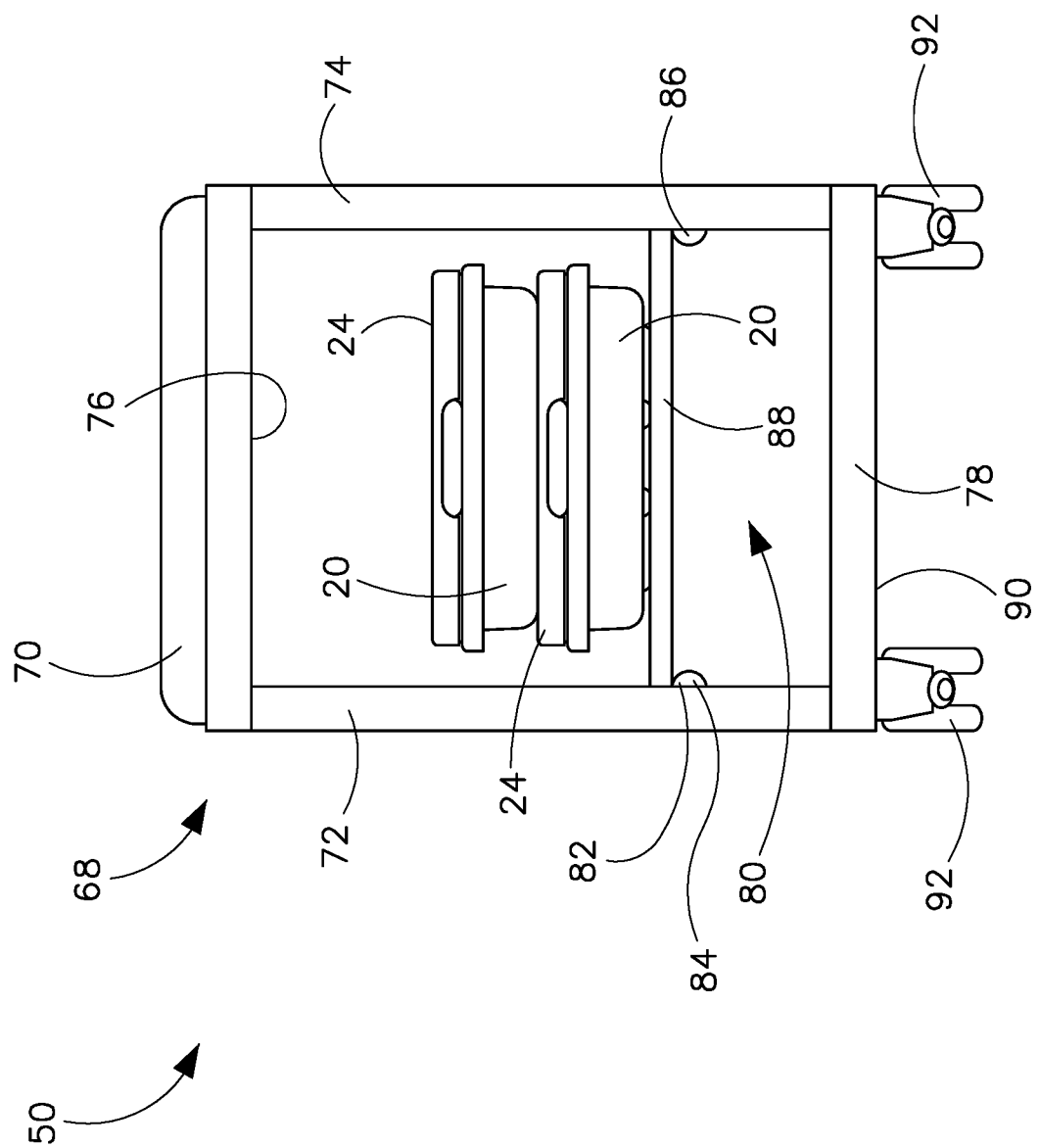
FIG. 31 illustrates trays and lids stacked together on a shelf of a cart.

The system includes a cart 68, as shown in FIG. 31. A suitable cart for use with the present application can be a CleanaScope™ Cart and/or a CleanaScope™ Advantage Cart available from Medivators Inc., MN, USA. Other suitable carts that are compatible with the tray and the lid can include SureStore® described in U.S. Pat. No. 9,421, 292, the entire disclosure of this patent is incorporated herein by reference, Transcope™ and/or Storascope™, available from Medivators Inc., MN, USA. The cart is configured to assist in the transportation and/or storage of one or more of the trays that store one or more endoscopes. It is to be understood that the cart is defined as a mobile storage unit. However, a cabinet which is defined as a static or stationary storage unit can alternatively be used. The cart can also be an endoscope washing and/or drying cart.

The cart includes a housing 70. The housing includes opposing side walls 72, 74 and top and bottom walls 76, 78. The cart can be in a rectangular configuration. An interior 80 of the housing comprises one or a plurality of slots 82, each configured to slidably receive the tray or a shelf 88. The slots are transverse relative to the opposing side walls. Each slot is defined by ledges 84, 86 that are in parallel orientation relative to each other. The cart can comprise one or more slots, such as 1 to about 12 slots.

In some embodiments, the stacked trays and lids can be placed on the shelf of the cart, as shown in FIG. 31. Alternatively, in some embodiments, the lidded trays are separated by the ledges of the slots, however, the ledges are configured in a manner that allows the trays and the lids to maintain a stacked configuration where the trays and the lids are locked to prevent lateral side to side movement.

In some embodiments, the bottom wall includes an exterior surface 90 that attaches to a plurality of wheels 92, such as caster wheels. The cart can include 4 or more wheels disposed at corners of the exterior surface. The cart can be washed and can be heat and chemical resistant.

Further, specific trays and specific carts can be tailored for specific endoscope suites in a medical facility and can be tailored for patient specific use.

It is to be understood that the tray engaged with the lid, liner and/or the cover and disposed with the cart for storage and/or transportation can reduce the number of receptacles used for endoscope reprocessing and delivery.

It is to be understood that in some embodiments, the tray can be a perforated tray having a plurality of apertures disposed on surfaces of the tray to facilitate drainage of fluids. These apertures disposed on the tray are described in U.S. Provisional Application Ser. No. 62/864,076, filed on Jun. 20, 2019 to Medivators Inc. The entire disclosure of this application is incorporated herein by reference.

The cart can be made from various materials, including, but not limited to metals, such as for example, stainless steel alloys, commercially pure titanium, titanium alloys, Grade 5 titanium, cobalt-chrome alloys, or combinations thereof. In some embodiments, the cart can be made from thermoplastic materials and/or the materials described above with regard to the tray. In some embodiments, the cart is configured to be heat and chemical resistant.

In some embodiments, contaminants can include, but are not limited to, biological contaminants such as microorganisms including bacteria, viruses, yeasts, molds and parasites; air borne contaminants such as airborne microbes; and/or chemical contaminants. In some embodiments, bacterial can include, but is not limited to *Escherichia coli, Klebsiella* species, *Enterobacter* species, enterococci, *Pseudomonas aeruginosa* and *Salmonella* species.

Methods and Kits

A method of using stackable endoscope storage trays is provided. The method comprises placing a first endoscope within a first tray, the first tray comprising an interior for storage of the first endoscope, the first tray having a first lid configured to cover the first tray, the first lid having an exterior surface having a recess and/or projection, and the first tray having a bottom exterior surface having a recess and/or projection; covering the first tray with the first lid; placing a second endoscope within a second tray, the second tray comprising an interior for storage of the second endoscope, the second tray having a second lid configured to cover the second tray, the second lid having an exterior surface having a recess and/or projection, and the second tray having a bottom exterior surface having a recess and/or projection; covering the second tray with the second lid; and stacking the recess and/or projection of the bottom exterior surface of the second tray on the recess and/or projection of the exterior surface of the first lid to mate the second tray with the first lid to reduce side to side movement of the first tray and the second tray. It is to be understood that the first and second trays are trays 20 and the first and second lids are lids 24 described above with regard to FIGS. 1-21.

In some embodiments, the exterior surface of the first lid and/or the second lid can comprise a plurality of recesses and/or projections arranged in a pattern and are configured to mate with a plurality of recesses and/or projections of the bottom exterior surface of the first tray and/or the second tray that are also arranged in a pattern. In some embodiments, the first tray and/or the second tray is configured to engage with a disposable liner. In some embodiments, the first tray and/or the second tray comprises a flexible cover configured to enclose or partially enclose a lidded first tray and/or second tray.

In some embodiments, the recess and/or projection of the first tray and the second tray and/or the recess and/or projection of the first lid and the second lid are vacuum formed or injection molded. In some embodiments, the first endoscope and the second endoscope are reprocessed and stored in the interior of the first tray and the second tray. In some embodiments, the first tray and the second tray are stored in a washer compatible cart.

In some embodiments, components of the system described above may be made by injection molding, compression molding, blow molding, thermoforming, die pressing, slip casting, electrochemical machining, laser cutting, water-jet machining, electrophoretic deposition, powder injection molding, sand casting, shell mold casting, plaster-mold casting, investment casting, vacuum casting, permanent-mold casting, slush casting, pressure casting, die casting, centrifugal casting, squeeze casting, rolling, forging, swaging, extrusion, shearing, spinning, or combinations thereof.

In some embodiments, the components of the system may be formed by 3D printing. The terms "three-dimensional printing system," "three-dimensional printer," and "printing," describe various solid freeform fabrication techniques for making three-dimensional articles or objects by selective deposition, jetting, fused deposition modeling, multi-jet modeling, and other additive manufacturing techniques now known in the art or that may be known in the future that use a build material or ink to fabricate three-dimensional objects.

Instructions in the form of schematics encompassing any of the embodiments disclosed herein may be given to a computer to be carried out by a 3D printer. In some embodiments, components of the system may be color coded to signify various properties.

Components of the system may be sterilizable. In various embodiments, one or more components of the system are sterilized by gas sterilization, such as, for example, with ethylene oxide or steam sterilization.

In various embodiments, one or more components of the system are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the system. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

In various embodiments, a kit or system is provided that may include additional parts along with one or more trays and lids combined together to be used with the cart. The kit may include one or more trays in a first compartment. A second compartment may include one or more lids. A third compartment may include one or more liners. A fourth compartment may include one or more covers. A fifth compartment may include cleaning solutions, gloves and other procedural supplies for performing cleaning of the endoscope, as well as an instruction booklet or notification of a website where instructions for using the kit or system can be located. Each component of the system or kit may be separately packaged in a plastic pouch. A cover of the kit may include illustrations of the use of the cover and a clear plastic cover may be placed over the compartments to maintain sterility.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. An endoscope storage tray comprising an interior for storage of an endoscope, the tray having a lid configured to cover the tray, the lid having an exterior surface having a plurality of square shaped projections, and the tray having a bottom exterior surface having a plurality of square shaped recesses such that the projections of the lid are configured to mate with the square shaped recesses of the bottom exterior surface of the tray, wherein the tray is re-usable and comprises a base and surrounding sidewalls upstanding therefrom and a peripheral lip disposed at least partially around the surrounding sidewalls and extending outwardly therefrom, the tray being formed of a semi-rigid polymeric material capable of withstanding repeated reprocessing and dimensioned to provide support for a flexible medical endoscope coiled in a stress-free state.

2. The endoscope tray of claim 1, wherein the lid mates with the recess of the bottom exterior surface of the tray when the tray is uncovered.

3. The endoscope tray of claim 1, wherein the tray comprises a puncture resistant flexible cover configured to enclose or partially enclose the tray.

4. The endoscope tray of claim 3, wherein the flexible cover is in a sheet or a bag configuration.

5. The endoscope tray of claim 3, wherein the flexible cover engages and partially encloses the tray with an elastic portion.

* * * * *